US012193710B2

(12) United States Patent
Lindekugel et al.

(10) Patent No.: US 12,193,710 B2
(45) Date of Patent: Jan. 14, 2025

(54) REUSABLE PUSH-ACTIVATED INTRAOSSEOUS ACCESS DEVICE

(71) Applicant: Bard Access Systems, Inc., Salt Lake City, UT (US)

(72) Inventors: Eric W. Lindekugel, Salt Lake City, UT (US); Daniel B. Blanchard, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/385,056

(22) Filed: Oct. 30, 2023

(65) Prior Publication Data
US 2024/0058036 A1 Feb. 22, 2024

Related U.S. Application Data

(62) Division of application No. 17/235,134, filed on Apr. 20, 2021, now Pat. No. 11,896,264.
(Continued)

(51) Int. Cl.
*A61B 17/34* (2006.01)
*A61B 17/16* (2006.01)
(Continued)

(52) U.S. Cl.
CPC ........ *A61B 17/3472* (2013.01); *A61B 17/162* (2013.01); *A61B 17/1626* (2013.01);
(Continued)

(58) Field of Classification Search
CPC ... A61B 17/16; A61B 17/162; A61B 17/1622; A61B 17/1624; A61B 17/1626;
(Continued)

(56) References Cited

U.S. PATENT DOCUMENTS 2,773,501 A 12/1956 Young
3,071,135 A 1/1963 Baldwin et al.
(Continued)

FOREIGN PATENT DOCUMENTS

CN 108742795 A 11/2018
CN 110547847 A 12/2019
(Continued)

OTHER PUBLICATIONS

U.S. Appl. No. 17/335,870, filed Jun. 1, 2021 Non-Final Office Action dated Nov. 15, 2023.
(Continued)

*Primary Examiner* — Eric S Gibson
(74) *Attorney, Agent, or Firm* — Rutan & Tucker LLP

(57) ABSTRACT

Push activated intraosseous (IO) access devices include replaceable and rechargeable or non-rechargeable battery packs, or spring driven devices. Intraosseous access devices often require training to ensure correct placement of the access device. The disclosed devices include an intuitive operation with a unidirectional activation and drive force application. The trigger can be both activated and deactivated automatically to prevent premature activation and prevent "backwalling". The device can include various indicators to further guide a user in placing the device correctly, with little or no training. Devices can further include replaceable battery packs to ensure a full charge is available when the device is used, and to provide a multi-use device that requires less storage.

19 Claims, 11 Drawing Sheets

Related U.S. Application Data

(60) Provisional application No. 63/013,371, filed on Apr. 21, 2020.

(51) Int. Cl.
 *A61B 17/00* (2006.01)
 *A61B 90/00* (2016.01)

(52) U.S. Cl.
 CPC ............ *A61B 17/1628* (2013.01); *A61B 2017/00075* (2013.01); *A61B 2017/00115* (2013.01); *A61B 2017/00132* (2013.01); *A61B 2017/00734* (2013.01); *A61B 2090/064* (2016.02); *A61B 2090/0807* (2016.02)

(58) Field of Classification Search
 CPC ... A61B 17/1628; A61B 17/164; A61B 17/34; A61B 17/3472
 See application file for complete search history.

(56) References Cited

U.S. PATENT DOCUMENTS

| | | | |
|---|---|---|---|
| 3,734,207 A | 5/1973 | Fishbein |
| 3,804,544 A | 4/1974 | Adams |
| 3,811,442 A | 5/1974 | Maroth |
| 3,815,605 A | 6/1974 | Schmidt et al. |
| 3,991,765 A | 11/1976 | Cohen |
| 4,266,555 A | 5/1981 | Jamshidi |
| 4,314,565 A | 2/1982 | Lee |
| 4,381,777 A | 5/1983 | Garnier |
| 4,383,530 A | 5/1983 | Bruno |
| 4,736,742 A | 4/1988 | Alexson et al. |
| 4,787,893 A | 11/1988 | Villette |
| 4,889,529 A | 12/1989 | Haindl |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,332,398 A | 7/1994 | Miller et al. |
| 5,364,367 A | 11/1994 | Banks et al. |
| 5,372,583 A | 12/1994 | Roberts et al. |
| 5,406,940 A | 4/1995 | Melzer et al. |
| 5,451,210 A | 9/1995 | Kramer et al. |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,667,509 A | 9/1997 | Westin |
| 5,688,249 A | 11/1997 | Chang et al. |
| 5,694,019 A | 12/1997 | Uchida et al. |
| 5,779,708 A | 7/1998 | Wu |
| 5,817,052 A | 10/1998 | Johnson et al. |
| 5,853,393 A | 12/1998 | Bogert |
| 5,868,711 A | 2/1999 | Kramer et al. |
| 5,885,293 A | 3/1999 | McDevitt |
| 5,927,976 A | 7/1999 | Wu |
| 5,960,797 A | 10/1999 | Kramer et al. |
| 5,967,143 A | 10/1999 | Klappenberger |
| 6,018,227 A | 1/2000 | Kumar et al. |
| 6,056,165 A | 5/2000 | Speranza |
| 6,104,162 A | 8/2000 | Sainsbury et al. |
| 6,117,108 A | 9/2000 | Woehr et al. |
| 6,135,769 A | 10/2000 | Kwan |
| 6,159,161 A | 12/2000 | Hodosh |
| 6,199,664 B1 | 3/2001 | Tkaczyk et al. |
| 6,210,373 B1 | 4/2001 | Allmon |
| 6,228,088 B1 | 5/2001 | Miller et al. |
| 6,247,928 B1 | 6/2001 | Meller et al. |
| 6,270,484 B1 | 8/2001 | Yoon |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,547,561 B2 | 4/2003 | Meller et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,997,907 B2 | 2/2006 | Safabash et al. |
| 7,112,191 B2 | 9/2006 | Daga |
| 7,135,031 B2 | 11/2006 | Flint |
| 7,214,208 B2 | 5/2007 | Vaillancourt et al. |
| 7,347,838 B2 | 3/2008 | Kulli |
| 7,347,840 B2 | 3/2008 | Findlay et al. |
| 7,407,493 B2 | 8/2008 | Cane' |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,502 B2 | 7/2011 | Baid |
| 8,038,038 B2 | 10/2011 | Hillhouse et al. |
| 8,038,664 B2 | 10/2011 | Miller et al. |
| 8,043,253 B2 | 10/2011 | Kraft et al. |
| 8,043,265 B2 | 10/2011 | Abe et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,235,945 B2 | 8/2012 | Baid |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,541 B2 | 3/2013 | Messerly et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |

(56) References Cited

U.S. PATENT DOCUMENTS

| | | |
|---|---|---|
| 8,535,271 B2 | 9/2013 | Fuchs et al. |
| 8,562,615 B2 | 10/2013 | Browne et al. |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,894,654 B2 * | 11/2014 | Anderson ............ B25B 21/002 |
| | | 173/176 |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 * | 4/2017 | Nino .................. A61B 17/3496 |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 * | 10/2018 | Morgan ............ A61B 10/025 |
| 10,092,706 B2 | 10/2018 | Denzer et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| D898,908 S | 10/2020 | Denzer et al. |
| 10,893,887 B2 | 1/2021 | Blanchard |
| 10,973,532 B2 | 4/2021 | Miller et al. |
| 10,973,545 B2 | 4/2021 | Miller et al. |
| 10,980,522 B2 | 4/2021 | Muse |
| 11,298,202 B2 | 4/2022 | Miller et al. |
| 11,896,264 B2 * | 2/2024 | Lindekugel ........ A61B 17/162 |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1 | 7/2005 | Miller |
| 2006/0015066 A1 | 1/2006 | Turieo et al. |
| 2006/0025723 A1 | 2/2006 | Ballarini |
| 2006/0058826 A1 | 3/2006 | Evans et al. |
| 2007/0049945 A1 | 3/2007 | Miller |
| 2007/0096690 A1 | 5/2007 | Casalena et al. |
| 2007/0191772 A1 | 8/2007 | Wojcik |
| 2007/0270775 A1 | 11/2007 | Miller et al. |
| 2007/0276352 A1 | 11/2007 | Crocker et al. |
| 2007/0282344 A1 | 12/2007 | Yedlicka et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0194446 A1 | 8/2009 | Miller et al. |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0174243 A1 | 7/2010 | McKay |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0202065 A1 | 8/2011 | Takizawa et al. |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1 | 6/2014 | Mark |
| 2014/0188133 A1 | 7/2014 | Misener |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Arsen et al. |
| 2014/0276839 A1 | 9/2014 | Forman et al. |

(56) References Cited

U.S. PATENT DOCUMENTS

| | | |
|---|---|---|
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1* | 8/2015 | Morgan ............ A61B 17/3476 604/272 |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2015/0367487 A1* | 12/2015 | Nino ............... A61B 17/8875 81/473 |
| 2016/0022282 A1 | 1/2016 | Miller et al. |
| 2016/0022284 A1 | 1/2016 | Lele et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1 | 10/2016 | Victor et al. |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1 | 6/2018 | Aeschlimann et al. |
| 2018/0154112 A1 | 6/2018 | Chan et al. |
| 2018/0221003 A1 | 8/2018 | Hibner et al. |
| 2018/0228509 A1 | 8/2018 | Fojtik |
| 2018/0242982 A1 | 8/2018 | Laughlin et al. |
| 2019/0059986 A1 | 2/2019 | Shelton, IV et al. |
| 2019/0069812 A1 | 3/2019 | Isaacson et al. |
| 2019/0083753 A1* | 3/2019 | Chu ................. A61B 17/3421 |
| 2019/0150954 A1 | 5/2019 | Xie |
| 2019/0175220 A1 | 6/2019 | Coppedge et al. |
| 2019/0282244 A1* | 9/2019 | Muse ............... A61B 17/1626 |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2020/0297382 A1 | 9/2020 | Coppedge et al. |
| 2020/0297452 A1 | 9/2020 | Coppedge et al. |
| 2020/0337782 A1 | 10/2020 | Glassman et al. |
| 2021/0015529 A1 | 1/2021 | Fenton, Jr. et al. |
| 2021/0093357 A1* | 4/2021 | Pett ................. A61B 17/3472 |
| 2021/0093358 A1 | 4/2021 | Lindekugel et al. |
| 2021/0113251 A1 | 4/2021 | Vogt et al. |
| 2021/0282812 A1 | 9/2021 | Tierney et al. |
| 2021/0322055 A1* | 10/2021 | Lindekugel ........ A61B 17/1626 |
| 2021/0375445 A1* | 12/2021 | Lindekugel ............ H04W 4/38 |
| 2021/0393337 A1 | 12/2021 | Zucker |
| 2022/0240976 A1 | 8/2022 | Pett et al. |
| 2022/0249104 A1 | 8/2022 | Pett et al. |
| 2023/0106545 A1 | 4/2023 | Pett et al. |
| 2023/0285049 A1 | 9/2023 | Howell |
| 2023/0414251 A1 | 12/2023 | Pett et al. |
| 2024/0206887 A1 | 6/2024 | Pett et al. |
| 2024/0261554 A1 | 8/2024 | Akerele-Ale et al. |
| 2024/0277375 A1 | 8/2024 | Lindekugel et al. |

FOREIGN PATENT DOCUMENTS

| | | |
|---|---|---|
| EP | 0923961 A1 | 6/1999 |
| EP | 3687024 A1 | 7/2020 |
| ES | 2390297 A1 | 11/2012 |
| FR | 2581548 A1 | 11/1986 |
| JP | 2018509969 A | 4/2018 |
| KR | 20090006621 A | 1/2009 |
| WO | 1997024151 A1 | 7/1997 |
| WO | 1998052638 A3 | 2/1999 |
| WO | 05041790 A2 | 5/2005 |
| WO | 2005046769 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011070593 A1 | 6/2011 |
| WO | 2011097311 A2 | 8/2011 |
| WO | 2011139294 A1 | 11/2011 |
| WO | 2013003885 A2 | 1/2013 |
| WO | 2013009901 A2 | 1/2013 |
| WO | 2013173360 A1 | 11/2013 |
| WO | 2014075165 A1 | 5/2014 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015061370 A1 | 4/2015 |
| WO | 2015177612 A1 | 11/2015 |
| WO | 2016033016 A1 | 3/2016 |
| WO | 16053834 A1 | 4/2016 |
| WO | 2016085973 A1 | 6/2016 |
| WO | 2016163939 A1 | 10/2016 |
| WO | 2018006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019164990 A1 | 8/2019 |
| WO | 2021011795 A1 | 1/2021 |
| WO | 2021016122 A1 | 1/2021 |
| WO | 2021062038 A1 | 4/2021 |
| WO | 2021062385 A1 | 4/2021 |
| WO | 2021062394 A1 | 4/2021 |
| WO | 2022165232 A1 | 8/2022 |

(56) References Cited

FOREIGN PATENT DOCUMENTS

| | | |
|---|---|---|
| WO | 2022170269 A1 | 8/2022 |
| WO | 2023177634 A1 | 9/2023 |

OTHER PUBLICATIONS

U.S. Appl. No. 17/337,100, filed Jun. 2, 2021 Final Office Action dated Nov. 21, 2023.
U.S. Appl. No. 17/337,100, filed Jun. 2, 2021 Notice of Allowance dated Jan. 24, 2024.
U.S. Appl. No. 17/469,613, filed Sep. 8, 2021 Non-Final Office Action dated Jan. 19, 2024.
U.S. Appl. No. 17/863,898, filed Jul. 13, 2022 Final Office Action dated Nov. 22, 2023.
Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.
EP 19757667.1 filed Sep. 18, 2020 Extended European Search Report dated Oct. 22, 2021.
EP 20867024.0 filed Apr. 21, 2022 Extended European Search Report dated Aug. 8, 2023.
EP 20868351.6 filed Apr. 21, 2022 Extended European Search Report dated Aug. 10, 2023.
EP 23166984.7 filed Apr. 6, 2023 Extended European Search Report dated Jul. 5, 2023.
PCT/US2019/018828 filed Feb. 20, 2019 International Preliminary Report on Patentability dated Aug. 27, 2020.
PCT/US2019/018828 filed Feb. 20, 2019 International Search Report and Written Opinion dated Jun. 13, 2019.
PCT/US2020/053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
PCT/US2021/035232 filed Jun. 1, 2021 International Search Report and Written Opinion dated Oct. 19, 2021.
PCT/US2021/046573 filed Aug. 18, 2021 International Search Report and Written Opinion dated Nov. 30, 2021.
PCT/US2021/047378 filed Aug. 24, 2021 International Search Report and Written Opinion dated Nov. 17, 2021.
PCT/US2021/048542 filed Aug. 31, 2021 International Search Report and Written Opinion dated Dec. 9, 2021.
PCT/US2021/049475 filed Sep. 8, 2021 International Search Report and Written Opinion dated Dec. 9, 2021.
PCT/US2021/028114 filed Apr. 20, 2021 International Search Report and Written Opinion dated Jul. 12, 2021.
PCT/US2021/035475 filed Jun. 2, 2021 International Search Report and Written Opinion dated Sep. 17, 2021.
PCT/US2022/014391 filed Jan. 28, 2022 International Search Report and Written Opinion dated Apr. 14, 2022.
PCT/US2022/015686 filed Feb. 8, 2022 International Search Report and Written Opinion dated May 25, 2022.
PCT/US2023/015127 filed Mar. 13, 2023 International Search Report and Written Opinion dated Jun. 26, 2023.
U.S. Appl. No. 17/031,650, filed Sep. 24, 2020 Final Office Action dated Jul. 20, 2022.
U.S. Appl. No. 17/031,650, filed Sep. 24, 2020 Non-Final Office Action dated Jan. 19, 2022.
U.S. Appl. No. 17/031,650, filed Sep. 24, 2020 Notice of Allowance dated Oct. 12, 2022.
U.S. Appl. No. 17/035,272, filed Sep. 28, 2020 Non-Final Office Action dated Mar. 9, 2023.
U.S. Appl. No. 17/035,272, filed Sep. 28, 2020 Notice of Allowance dated Jul. 7, 2023.
U.S. Appl. No. 17/035,272, filed Sep. 28, 2020 Restriction Requirement dated Dec. 9, 2022.
U.S. Appl. No. 17/035,336, filed Sep. 28, 2020 Notice of Allowance dated Jan. 11, 2023.
U.S. Appl. No. 17/035,336, filed Sep. 28, 2020 Restriction Requirement dated Jul. 26, 2022.
U.S. Appl. No. 17/235,134, filed Apr. 20, 2021 Non-Final Office Action dated Jun. 27, 2023.
U.S. Appl. No. 17/235,134, filed Apr. 20, 2021 Notice of Allowance dated Sep. 20, 2023.
U.S. Appl. No. 17/235,134, filed Apr. 20, 2021 Restriction Requirement dated Mar. 7, 2023.
U.S. Appl. No. 17/335,870, filed Jun. 1, 2021 Restriction Requirement dated Jul. 25, 2023.
U.S. Appl. No. 17/337,100, filed Jun. 2, 2021 Non-Final Office Action dated Jun. 2, 2023.
U.S. Appl. No. 17/469,613, filed Sep. 8, 2021 Restriction Requirement dated Oct. 23, 2023.
U.S. Appl. No. 17/667,291, filed Feb. 8, 2022 Non-Final Office Action dated Aug. 31, 2023.
U.S. Appl. No. 17/667,291, filed Feb. 8, 2022 Restriction Requirement dated May 31, 2023.
PCT/US2024/014241 filed Feb. 2, 2024 International Search Report and Written Opinion dated May 8, 2024.
U.S. Appl. No. 17/335,870, filed Jun. 1, 2021 Final Office Action dated Mar. 26, 2024.
U.S. Appl. No. 17/405,692, filed Aug. 18, 2021 Restriction Requirement dated May 10, 2024.
U.S. Appl. No. 18/075,269, filed Dec. 5, 2022 Non-Final Office Action dated Jun. 24, 2024.
U.S. Appl. No. 18/244,730, filed Sep. 11, 2023 Non-Final Office Action dated May 3, 2024.
U.S. Appl. No. 17/405,692, filed Aug. 18, 2021 Non-Final Office Action dated Sep. 6, 2024.
U.S. Appl. No. 17/410,863, filed Aug. 24, 2021 Non-Final Office Action dated Sep. 5, 2024.
U.S. Appl. No. 17/463,324, filed Aug. 31, 2021 Restriction Requirement dated Aug. 8, 2024.
U.S. Appl. No. 18/075,269, filed Dec. 5, 2022 Notice of Allowance dated Sep. 11, 2024.
U.S. Appl. No. 18/244,730, filed Sep. 11, 2023 Final Office Action dated Aug. 8, 2024.

* cited by examiner

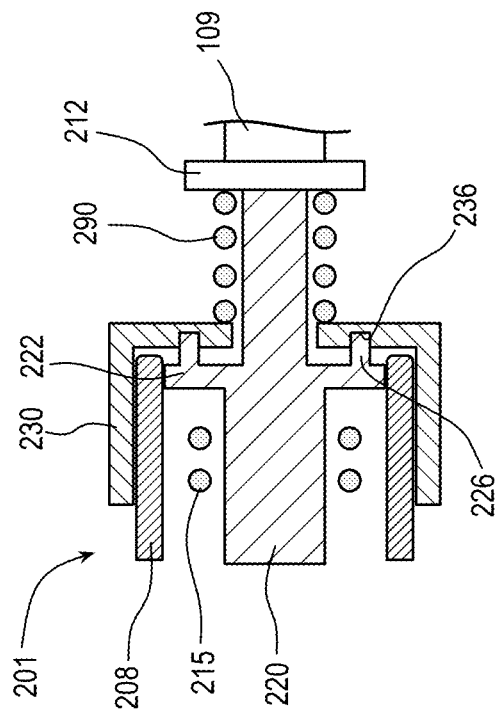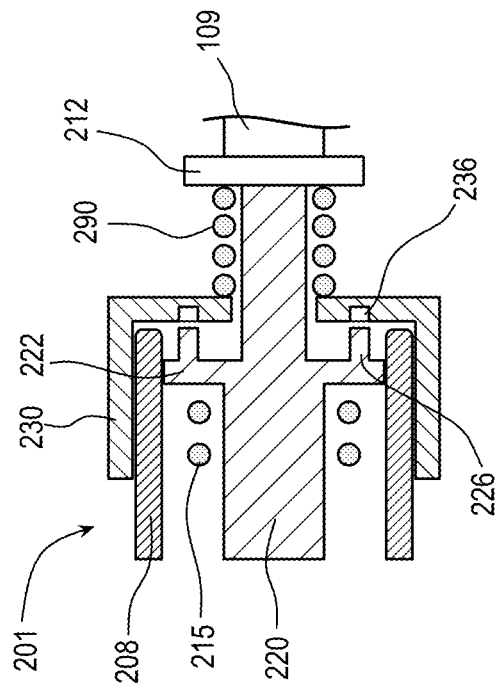
FIG. 5A    FIG. 5B
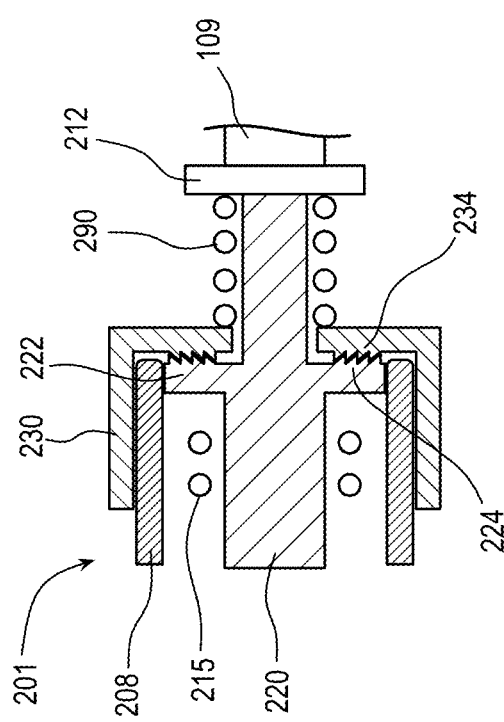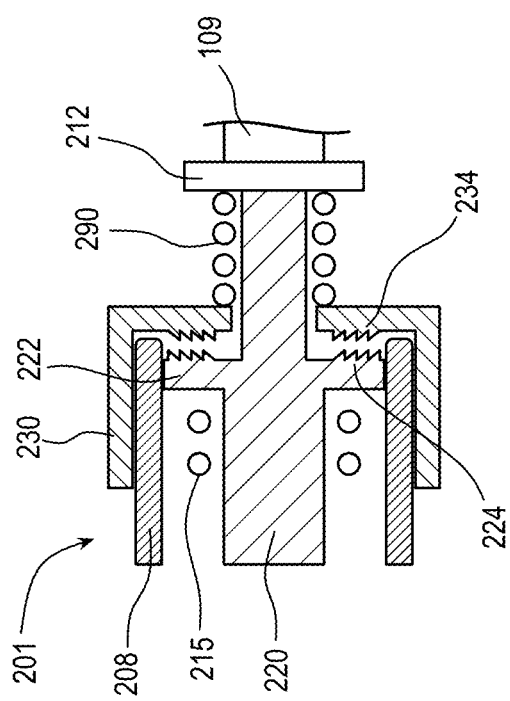
FIG. 5C    FIG. 5D

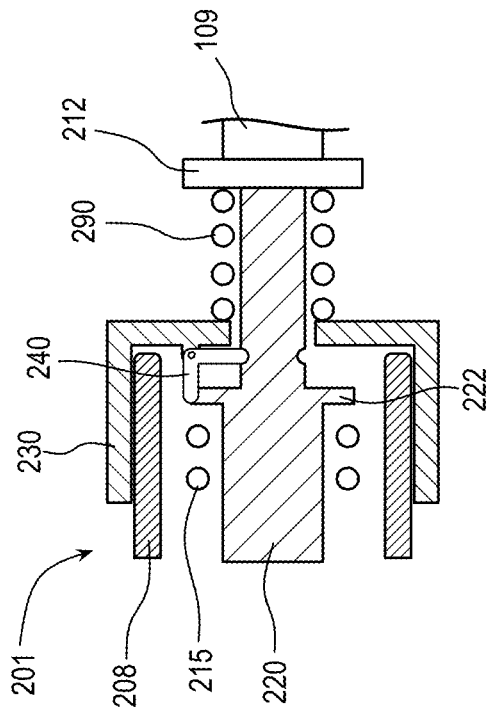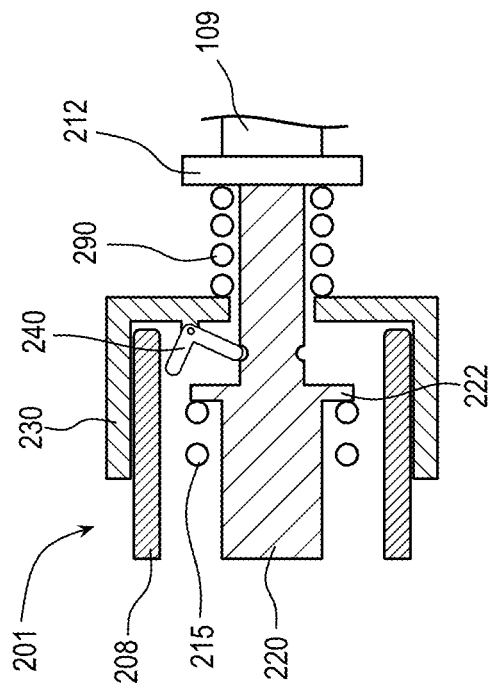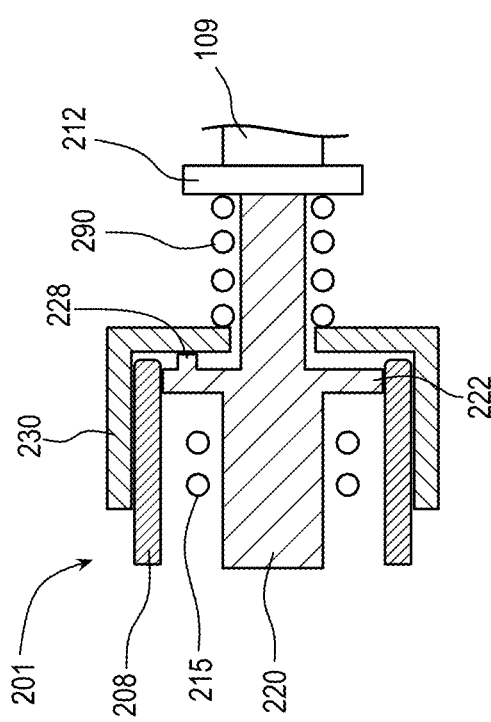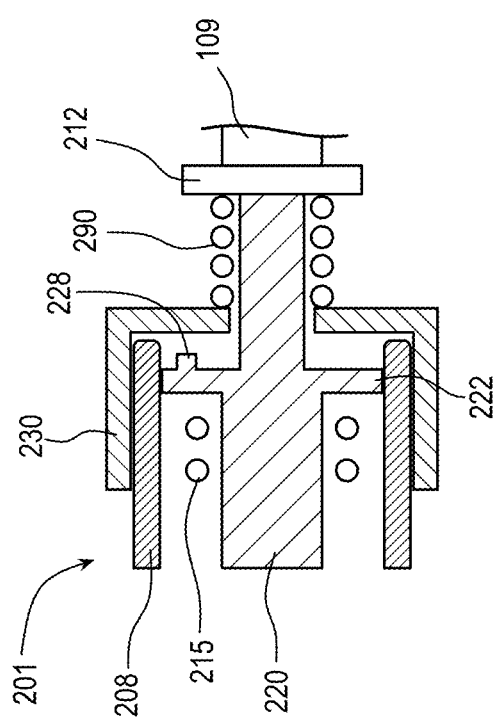

REUSABLE PUSH-ACTIVATED INTRAOSSEOUS ACCESS DEVICE

PRIORITY

This application is a division of U.S. patent application Ser. No. 17/235,134, filed Apr. 20, 2021, now U.S. Pat. No. 11,896,264, which claims the benefit of priority to U.S. Provisional Application No. 63/013,371, filed Apr. 21, 2020, each of which is incorporated by reference in its entirety into this application.

SUMMARY

Intraosseous access devices often require training to ensure correct placement of the access device. Users must coordinate the opposing actions of pulling proximally on a trigger, while applying sufficient distal driving force to penetrate the bone. Too little distal driving force results in osteonecrosis, where the needle tip rotates against the bone causing friction burns, instead of cutting into the bone as intended. Too much distal driving force can result in "back walling" where a needle penetrates a far wall of the bone. Further complications can arise when accessing bones of different sizes and density depending on the age and health of the patient. Moreover, IO access devices are often used in emergency situations where delays can be critical and fully trained users may not always be available.

Embodiments disclosed herein are directed to push activated intraosseous (IO) access devices, and methods thereof. Push activated IO devices provide an intuitive operation with a unidirectional activation and drive force application. Further the device is both activated and deactivated automatically to prevent premature activation, guide a correct amount of distal driving force, and prevent "backwalling." The device includes various indicators to further guide a user, who may have little or no training, in placing the device correctly. IO access devices disclosed herein further include replaceable battery packs, which may be either rechargeable or non-rechargeable, to ensure a full charge is available when the device is used, as well as providing a multi-use device that requires less storage space.

Disclosed herein is an intraosseous access device including, a housing, a trigger, and a drive train assembly, a portion of the drive train assembly slidably engaged with the housing, and configured to transition between a distal position, and a proximal position that actuates the trigger.

In some embodiments, the portion of the drive train assembly slidably engaged with the housing includes one of an electric motor, a gear assembly, a coupling structure, or an access assembly. The trigger is configured to connect a power supply with the drive train assembly when the trigger is actuated. The power supply is a battery pack disposed within the housing and configured to be removable and replaceable therefrom and wherein the battery pack is rechargeable or non-rechargeable. In some embodiments, the intraosseous access device further includes one of a force transducer, a variable speed sensor, a battery charge indicator, a timed stop sensor, or a trigger lock. The variable speed transducer is configured to modify a speed of the electric motor according to the amount of distal driving force applied to the intraosseous access device. The timed stop sensor is configured to stop the electric motor after a predetermined amount of time has elapsed. The trigger lock is transitionable between a locked position and an unlocked position, the trigger lock inhibiting the portion of the drive train assembly from transitioning to the proximal position when in the locked position.

In some embodiments, the intraosseous access device further includes a biasing member configured to bias the portion of the drive train assembly towards the distal position. A first force required to deform the biasing member and transition the portion of the drive train assembly from the distal position to the proximal position is greater than a second force required for a needle of an access assembly to penetrate a skin surface and less than a third force required for the needle to penetrate a bone cortex. In some embodiments, the intraosseous access device further includes a tensioning nut configured to adjust a tension of the biasing member. In some embodiments, the intraosseous access device further includes a force indicator configured to indicate an amount of force exerted on the biasing member. The force indicator includes one of a mechanical slider, a rotational dial, a series of graduated markings, or a series of LED lights.

Also disclosed is a method of placing an intraosseous access assembly including, providing an intraosseous access device having a driver, a drive train assembly, a portion of the drive train assembly transitionable between a first position and a second position, and an access assembly coupled to the drive train and including a needle, providing a first force to urge the access device distally until a tip of the needle penetrates a skin surface and contacts a bone cortex, providing a second force to urge the access device distally and transition the portion of the drive train assembly from a first position to a second position, rotating the access assembly, and drilling the needle through a bone cortex.

In some embodiments, the drive train includes one of a power source, an electronic control board, an electric motor, a gear assembly, or a coupling interface. The power source further includes a replaceable rechargeable or non-rechargeable battery pack. The drive train includes one of a drive spring, a drive spindle, a locking flange, or a coupling interface. In some embodiments, the method further includes an activation biasing member configured to bias the portion of the drive train assembly towards the first position, and wherein a force required to deform the activation biasing member is greater than the first force and less than second force. In some embodiments, the method further includes a tensioning nut configured to adjust a tension of the activation biasing member. In some embodiments, the method further includes a time out sensor configured to cease rotating the access assembly after a predetermined amount of time has elapsed.

Also disclosed is an access device including a driver housing, a drive spindle configured to rotate axially within the driver housing and configured to transition between a locked position and an unlocked position, a drive spring configured to rotate the drive spindle, and an access assembly coupled to the drive spindle.

In some embodiments, the access device further includes an activation biasing member configured bias the drive spindle to the locked position. A first force required to deform the activation biasing member and transition the drive spindle from the distal position to the proximal position is greater than a second force required for a needle of the access assembly to penetrate a skin surface and less than a third force required for the needle to penetrate a bone cortex. The activation biasing member is a compression spring and the first force is between 2 lbs and 4 lbs of force. In some embodiments, the access device further includes a tensioning nut threadably engaged with the driver housing, and configured to modify an amount of force required to deform the activation biasing member. The drive spindle further includes a locking flange configured to engage the driver housing and inhibit axial rotation when the drive spindle is in the locked position. The locking flange engages the driver housing with one of a plurality of ratchet teeth, a lug and detent, a frangible bridge, or a locking lever. The drive spring includes one of a torsion spring or a flat spring.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 5A-5H illustrate close-up details of a spring-driven intraosseous access device, in accordance with embodiments disclosed herein.

DESCRIPTION

Figure 1:
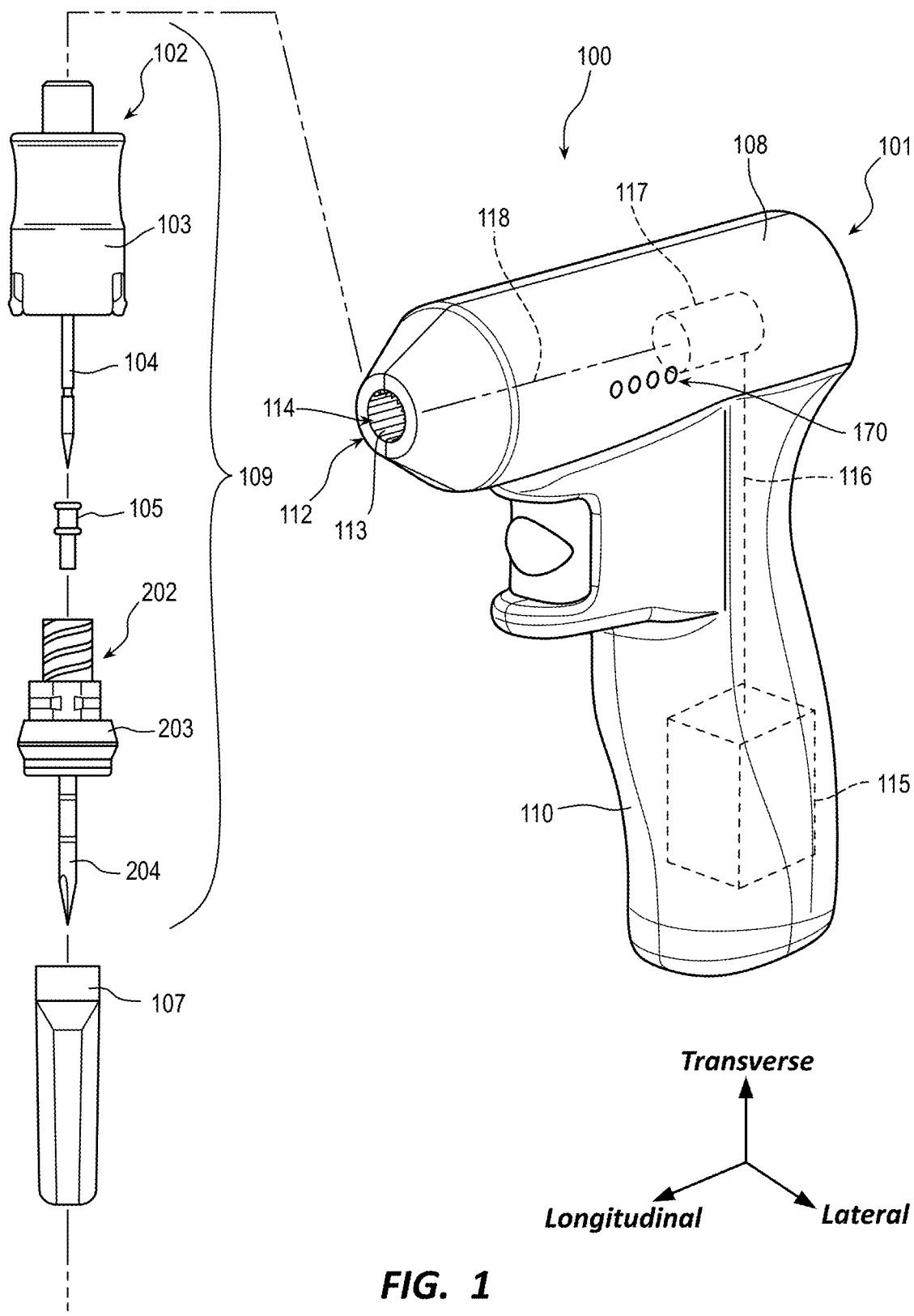
FIG. 1 illustrates an exploded view of an embodiment of an intraosseous access system, wherein an access assembly subset of the system is depicted slightly enlarged and in elevation, and an automated driver component is depicted in perspective, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

As shown in FIG. 1, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes.

As used herein, the term "spring" is considered to include any type of spring or biasing member that may store potential mechanical energy. Exemplary biasing members can include compression springs, extension springs, torsion springs, constant force springs, flat spring, flexible members, rubber rings, rubber band, leaf spring, V-spring, cantilever spring, volute spring, Belleville spring, gas spring, gravitypropelled biasing members, combinations thereof and the like, and are considered to fall within the scope of the present invention.

Unless defined otherwise, all technical and scientific terms used herein have the same meaning as commonly understood by those of ordinary skill in the art.

The present disclosure relates generally to intraosseous (IO) access devices, systems, and methods thereof. FIG. 1 shows an exploded view of an exemplary intraosseous access system ("system") 100, with some components thereof shown in elevation and another shown in perspective. In an embodiment, the intraosseous access system 100 can be used to penetrate skin and underlying hard bone ("bone cortex") for intraosseous access, such as, for example to access the marrow of the bone and/or a vasculature of the patient via a pathway through an interior of the bone ("medullary cavity").

In an embodiment, the system 100 includes a driver 101 and an access assembly 109. The driver 101 can be used to rotate the access assembly 109 and "drill" a needle 204 into the bone of a patient. In embodiments, the driver 101 can be automated or manual. As shown, the driver 101 is an automated driver 101. For example, the automated driver 101 can be a drill that achieves high rotational speeds. In an embodiment, the intraosseous access system 100 can further include an obturator assembly 102, a shield 105, and a needle assembly 202, which may be referred to, collectively, as the access assembly 109. The needle assembly 202 can include an access needle ("needle") 204 supported by a needle hub 203, as described in more detail herein. In an embodiment, the obturator assembly 102 includes an obturator 104. However, in some embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, and the like. Accordingly, the obturator assembly 102 may be referred to more generally as an elongated medical instrument assembly. In like manner, the obturator 104 may be referred to more generally as an elongated medical instrument.

In an embodiment, the obturator assembly 102 includes a coupling hub 103 that is attached to the obturator 104 in any suitable manner (e.g., one or more adhesives or overmolding). The coupling hub 103 can be configured to interface with the driver 101, as further discussed below. The coupling hub 103 may alternatively be referred to as an obturator hub 103 or, more generally, as an elongated instrument hub 103. In an embodiment, the shield 105 is configured to couple with the obturator 104 to prevent accidental needle stick injuries when the obturator is removed after placement of the needle 204.

In an embodiment, the needle assembly 202 includes a needle 204. However, in some embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In an embodiment, the needle assembly 202 includes a needle hub 203 that is attached to the needle 204 in any suitable manner. The needle hub 203 can be configured to couple with the obturator hub 103 and may thereby be coupled with the driver 101, as further discussed below. The needle hub 203 may alternatively be referred to as a cannula hub 203. In an embodiment, a cap 107 may be provided to cover at least a distal portion of the needle 204 and the obturator 104 prior to use of the access assembly 109. For example, in an embodiment, a proximal end of the cap 107 can be coupled to the obturator hub 103.

With continued reference to FIG. 1, the driver 101 may take any suitable form. The driver 101 may include a handle 110 that may be gripped by a single hand of a user. In an embodiment, the driver 101 further includes a coupling interface 112, which is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are also contemplated.

The driver 101 can include an energy source 115 of any suitable variety that is configured to energize the rotational movement of the coupling interface 112. For example, in some embodiments, the energy source 115 may comprise one or more batteries that provide electrical power for the driver 101. In some embodiments, the energy source 115 can comprise one or more springs (e.g., a coiled spring, flat spring, or the like) or other biasing member that may store potential mechanical energy that may be released upon actuation of the driver 101.

The energy source 115 may be coupled with the coupling interface 112 in any suitable manner. For example, in an embodiment, the driver 101 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage to the gear assembly 117. The driver 101 can include a mechanical coupling of any suitable variety to couple the gear assembly 117 with the coupling interface 112. In other embodiments, the gear assembly 117 may be omitted.

Further details and embodiments of the intraosseous access system 100 can be found in WO 2018/075694, WO 2018/165334, WO 2018/165339, and US 2018/0116693, each of which is incorporated by reference in its entirety into this application.

Figure 2A:
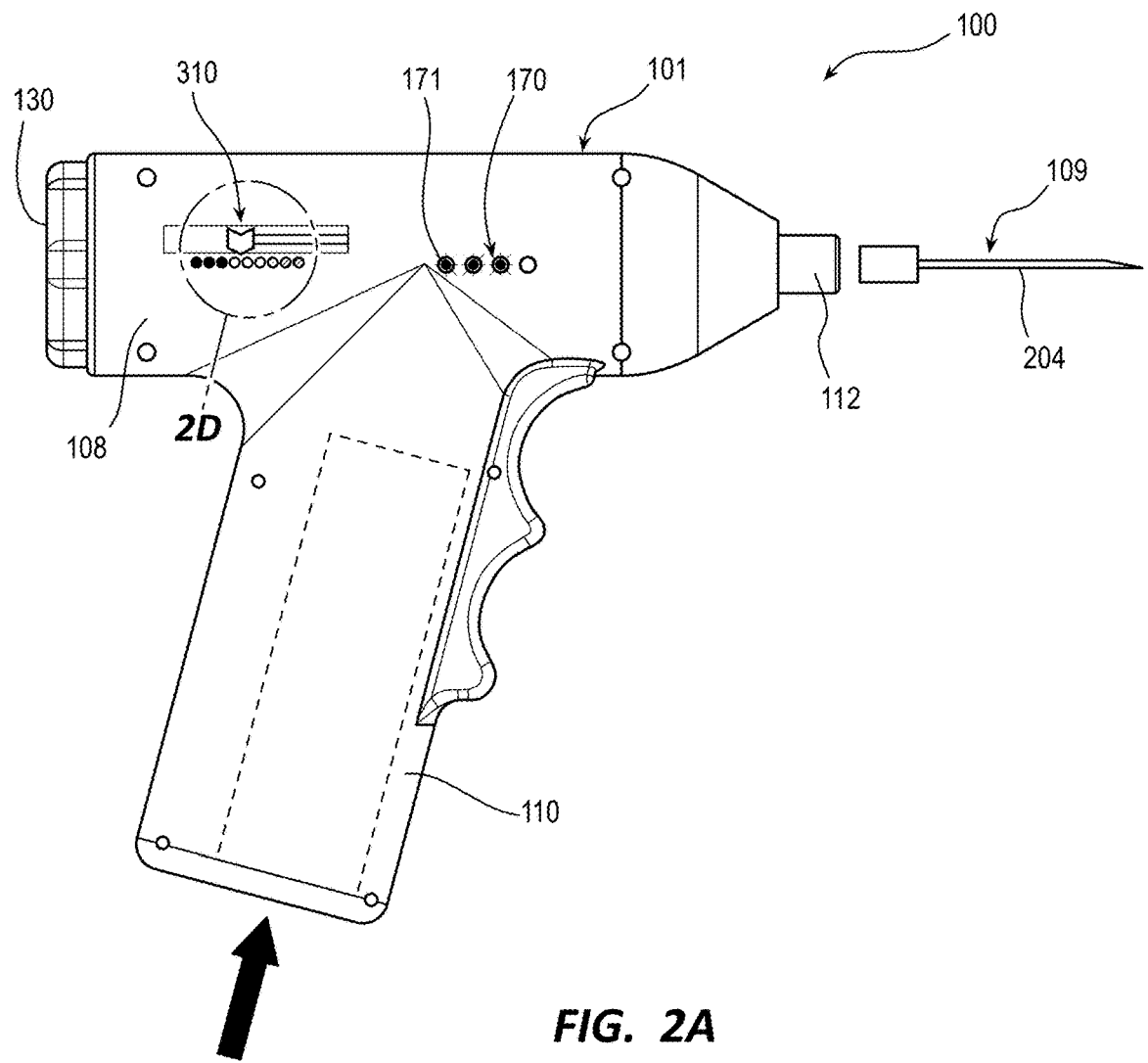
FIG. 2A illustrates a side view of an intraosseous access system, in accordance with embodiments disclosed herein.

FIG. 2A shows an embodiment of an intraosseous access device 100, including a driver 101 that includes a replaceable battery pack energy source ("battery pack") 115. In an embodiment the battery pack 115 is removable and replaceable with similar battery packs. In an embodiment, the battery pack 115 can either be rechargeable or non-rechargeable. Advantageously, this allows a user of the system 100 to ensure there is sufficient power when the system is deployed in a placement event. Further, during a placement event, should the power be depleted from the first battery pack, a user can replace the first battery pack with a second, fully charged battery pack and continue the access procedure without having to wait for the first battery pack to be charged. As discussed herein, intraosseous access devices are often used in emergency situations and are therefore kept in storage for extended periods of time before being rapidly deployed in a placement event. The replaceable battery pack 115 mitigates a user's concerns about there being sufficient charge during a placement event.

In an embodiment, the driver 101 includes a battery charge indicator 170. In an embodiment, the battery charge indicator 170 is disposed on the battery pack 115. The battery charge indicator 170 can include one or more LED lights, icons, or the like, that can turn on or off, change color, or combinations thereof, to indicate a level of charge of the battery pack 115. In an embodiment, the system 100 includes a charge indicator button 171 that a user can actuate to activate the battery charge indicator 170 and determine a charge level for the battery pack 115. Advantageously, the driver 101 and one or more replacement battery packs 115 can provide sufficient power for multiple uses while requiring less storage space compared with multiple, single-use, devices. Further, the overall costs are reduced by requiring only a replacement battery pack rather than requiring multiple, single-use access systems.

Figure 2D:
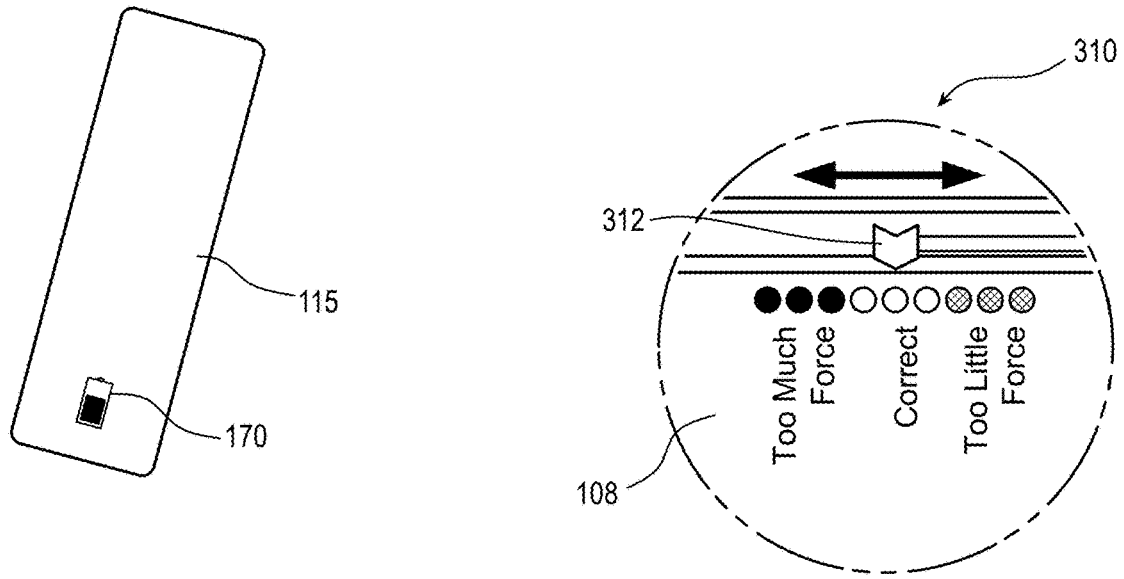
FIG. 2D illustrates close up detail of the device of FIG. 2A, in accordance with embodiments disclosed herein.
Figure 2B:
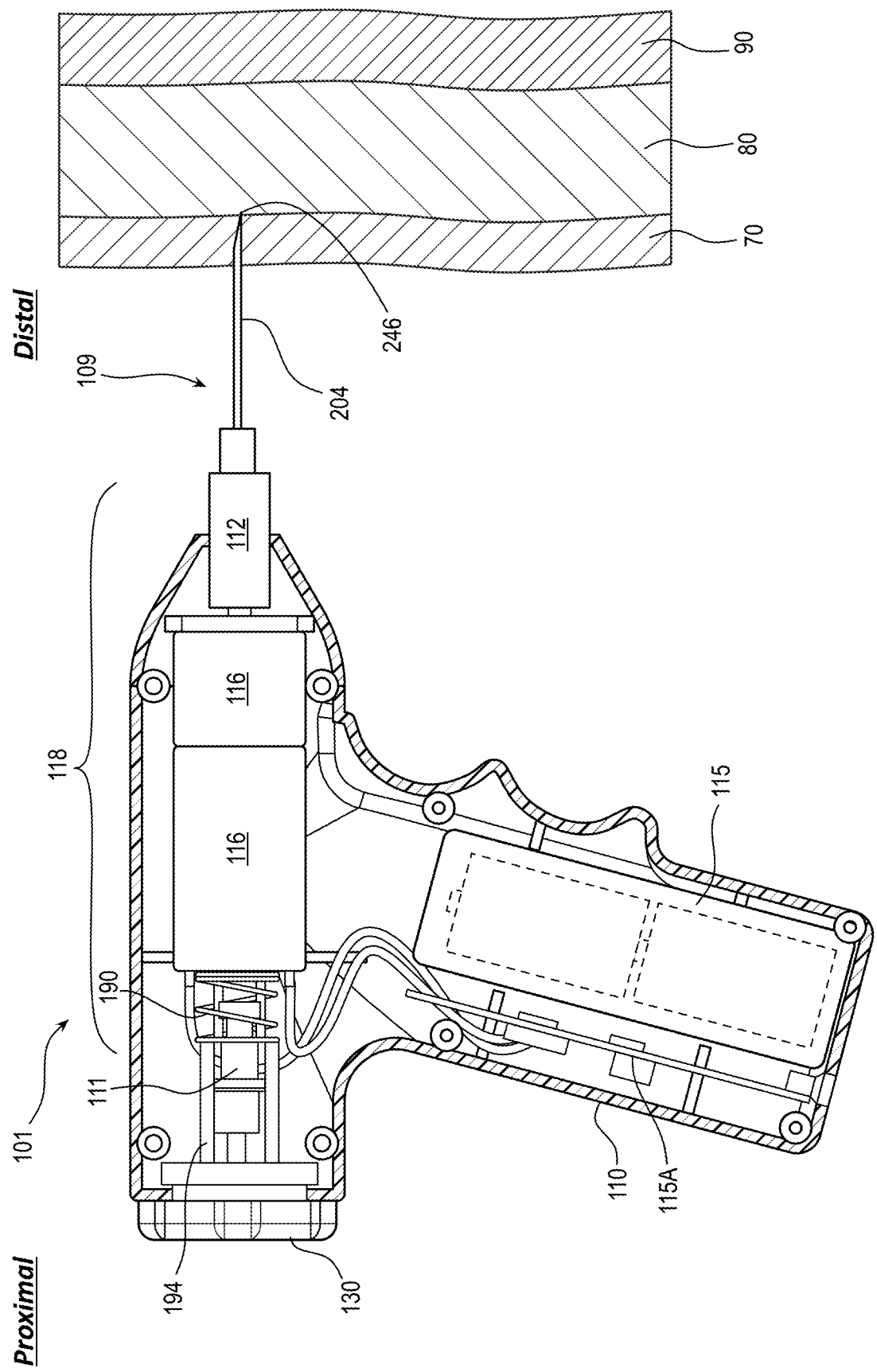
FIG. 2B illustrates a cross-sectional view of an intraosseous access system with an access assembly in a first, distal position, in accordance with embodiments disclosed herein.
Figure 2C:
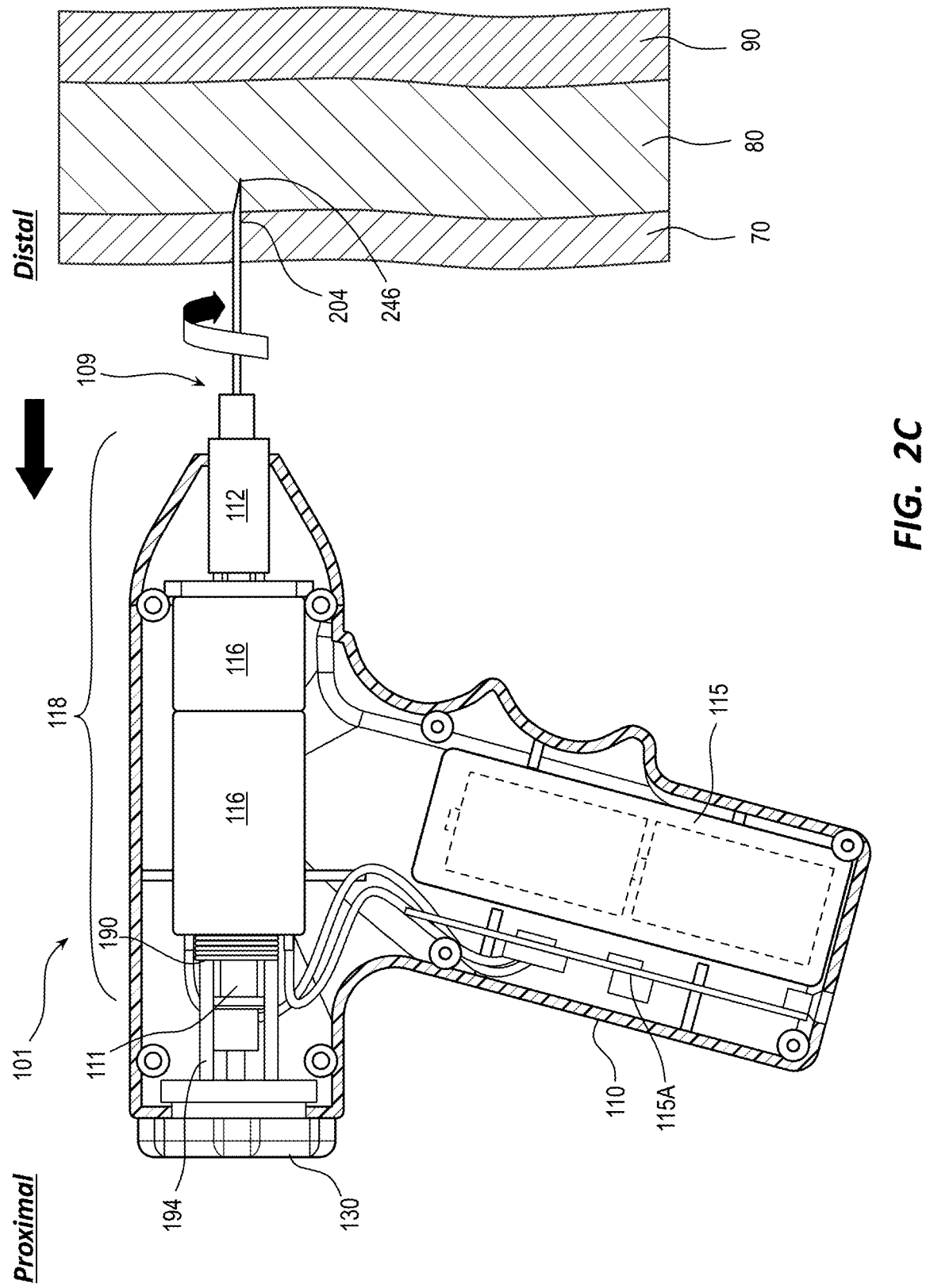
FIG. 2C illustrates a cross-sectional view of an intraosseous access system with an access assembly in a second, proximal position, in accordance with embodiments disclosed herein.

As shown in FIGS. 2B-2C, in an embodiment, the driver 101 includes a pressure activated trigger 111. The trigger 111 can be activated by an axial pressure on the access assembly 109. In an embodiment, a longitudinal pressure can depress the access assembly 109 in a proximal direction and activate the trigger 111, which activates the motor 116 and causes the access assembly 109 to rotate.

As used herein the battery pack 115 and any associated electronic control boards 115A, motor 116, associated gear assemblies 117, coupling structures 112, access assembly 109, or combinations thereof, can be collectively termed a drive train assembly ("drive train") 118. In an embodiment, the drive train 118 or a portion thereof, can be slidably engaged within a housing 108 of the driver 101. For example, as shown in FIGS. 2B-2C, a portion of the drive train 118, including the motor 116, coupling structures 112, and access assembly 109, can be slidably engaged along a longitudinal axis between a first, distal position (FIG. 2B) and a second, proximal position (FIG. 2C).

It will be appreciated, however, that any combination of components of the drive train 118 can be slidably engaged with the housing 108 with the remaining components of the drive train 118 remaining stationary. For example, in an embodiment, the portion of the drive train 118 slidably engaged with the housing 108 can include only the access assembly 109 with the remaining components remaining stationary. In an embodiment, all components of the drive train 118 can be slidably engaged with the housing 108. In an embodiment, a component of the drive train 118 can be further sub-divided with a first portion remaining stationary and second portion slidably engaged with the housing 108. For example, the coupling structures 112 can be made of a first piece slidably engaged with a second piece. As such, the portion of the drive train 118 that is slidably engaged with the housing 108 can include the access assembly 109 and a second piece of the coupling structures 112. These and other combinations of drive train assembly 118 are considered to fall within the scope of the present invention.

In an embodiment, a biasing member, for example an activation spring 190, can bias the slidable drive train 118, or portion thereof that is slidably engaged with the housing 108, towards a distal position. In an embodiment, a biasing member (e.g. a spring) can be disposed between a first portion and a second portion of the driver train 118, for example between the second piece of coupling structure 112 and the access assembly 109, to bias a portion of the drive train 118 towards a distal position. These and similar combinations of slidable drive train 118 are considered to fall within the scope of the present invention.

In an embodiment, the activation spring 190 can be a compression spring disposed within the driver 101, between the portion of the slidable drive train 118 and a distal end of the driver housing 108. However, as discussed herein, it will be appreciated that various other forms of biasing members are also contemplated, including compliant rubber discs, flexible metal tabs, or similar structures configured to bias the drive train 118 towards a distal position. In an embodiment, the driver 101 further includes a tensioning nut 130. In an embodiment, rotating the tensioning nut 130 can adjust the tension on the activation spring 190, and can modify the amount of force required to compress the activation spring 190 and activate the device, as discussed in more detail herein.

In an embodiment, a force required to compress the activation spring 190 can be between 2 lbs and 4 lbs, although greater or lesser forces are also contemplated. As shown in FIG. 2B, in an embodiment, a force required for the needle 204 to penetrate the skin tissues 70 can be less than a force required to compress activation spring 190. As such the activation spring 190 can maintain the drive train 118 in a proximal position as the needle penetrates the skin tissues 70. In an embodiment, a force required for the needle 204 to penetrate the bone cortex 80 can be greater than a force required to compress activation spring 190. As such, when the needle tip 246 contacts the bone cortex 80, a user can apply additional distal driving force to compress the activation spring 190 and transition the drive train 118 from the distal position (FIG. 2B) to the proximal position (FIG. 2C).

As shown in FIG. 2C, in the proximal position, the drive train 118 contacts the trigger 111, which activates the motor 116 and rotates the access assembly 109. The needle tip 246 then drills through the bone cortex 80 and accesses the medullary cavity 90. The density of the tissue within the medullary cavity 90 is less than the density of the bone cortex 80. As such, a force required for the needle 204 to penetrate the tissues of the medullary cavity 90 can be less than a force required to compress activation spring 190. When the needle tip 246 enters the medullary cavity 90, the force of the activation spring 190 transitions the drive train 118 back to the distal position. This disengages the trigger 111, stops the motor 116 and automatically stops any rotation of the access assembly 109.

In an embodiment, the driver 101 can further include a tensioning nut 130, which is configured to rotate and move a spring support 194 along a longitudinal axis. This can adjust the amount force required to transition the drive train 118 from the distal position to the proximal position. As such, the tension of the activation spring 190 can be adjusted depending on various factors including age of the patient, health condition of the patient, the density of the bone cortex 80, the density of the tissue within the medullary cavity 90, combinations thereof, or the like.

In an exemplary method of use, an intraosseous access system 100 is provided including a driver 101, an access assembly 109, and a replaceable battery 115, as described herein. In an embodiment, the access assembly 109 and/or the replaceable battery 115 are provided pre-loaded in the driver 101. In an embodiment the access assembly 109 and/or the replaceable battery 115 are provided separately and the user can load the access assembly 109 and/or the replaceable battery 115 to the driver 101 prior to use. The user can check a charge level of the battery 115 using battery level indicator 170. If necessary the user can replace the battery 115 with a fully charged battery 115. In an embodiment, the system 100 can further include a cap 107 to protect the needle 204 of the access assembly 109.

The user can position a tip 246 of the needle 204 at the insertion site and apply a distal driving force to urge the driver 101 in a distal direction. As described herein, the activation spring 190 is configured to maintain the driver train 118 in a distal position as the needle 204 is urged through the skin surface tissues 70. The distal tip 246 of the needle 204 then contacts the hard bone cortex 80 which inhibits further distal advancement. The user continues to urge the driver 101 distally with sufficient force to overcome the force of the activation spring 190. This causes the drive train 118 to slide proximally, relative to the driver 101, and activate the trigger 111. The trigger 111 activates the motor 116 which causes the access assembly 109 to rotate and drill the needle 204 through the bone cortex 80. When the needle tip 246 penetrates through the bone cortex 80 and into the medullary cavity 90, the activation spring 190 can transition the drive train 118 back to the distal position since the force of the activation spring is greater than a force required to penetrate the needle 204 through tissues of the medullary cavity 90. In the distal position, the trigger 111 is disengaged, which disengages the motor 116 and ceases rotation of the access assembly 109.

Advantageously, the system 100 provides an intuitive function that only requires a single directional force to be applied to start the placement event, i.e. start drilling, compared with pulling a "pistol-style" trigger in a proximal direction while applying a driving force in a distal direction. Further, the activation spring 190 can be configured to deform and activate the device 100 automatically when the correct level of distal driving force is applied. A user can progressively increase the amount of distal driving force until the activation spring 190 compresses and activates the system 100, guiding the user towards a correct level of distal driving force.

Further still, the activation spring 190 can be configured to deactivate the device 100 automatically either when the user removes the distal driving force or when the needle 204 accesses medullary cavity 90. The automatic deactivation can indicate to a user of successful placement. This is of particular importance to prevent "back walling" which can lead to various complications. Further, the automatic deactivation of the device can act as a safety feature, deactivating the device if the device is removed from the insertion site. In an embodiment, the drive train 118 can also be configured to apply the correct torque and rotational speed for fast and effective access.

In an embodiment, the system 100 can be configured to modify the amount of torque and/or rotational speed based on the amount distal driving force applied. As such the system 100 can be configured to guide a user to deliver the correct balance of distal driving force, torque, and rotational speed for an intuitive, fast and efficient IO access placement. A user thereby requires little or no training to use the system 100. This is of particular importance intraosseous access devices are often used within emergency situations where speed of placement is important, and users may not necessarily have had any prior training.

Figure 3:
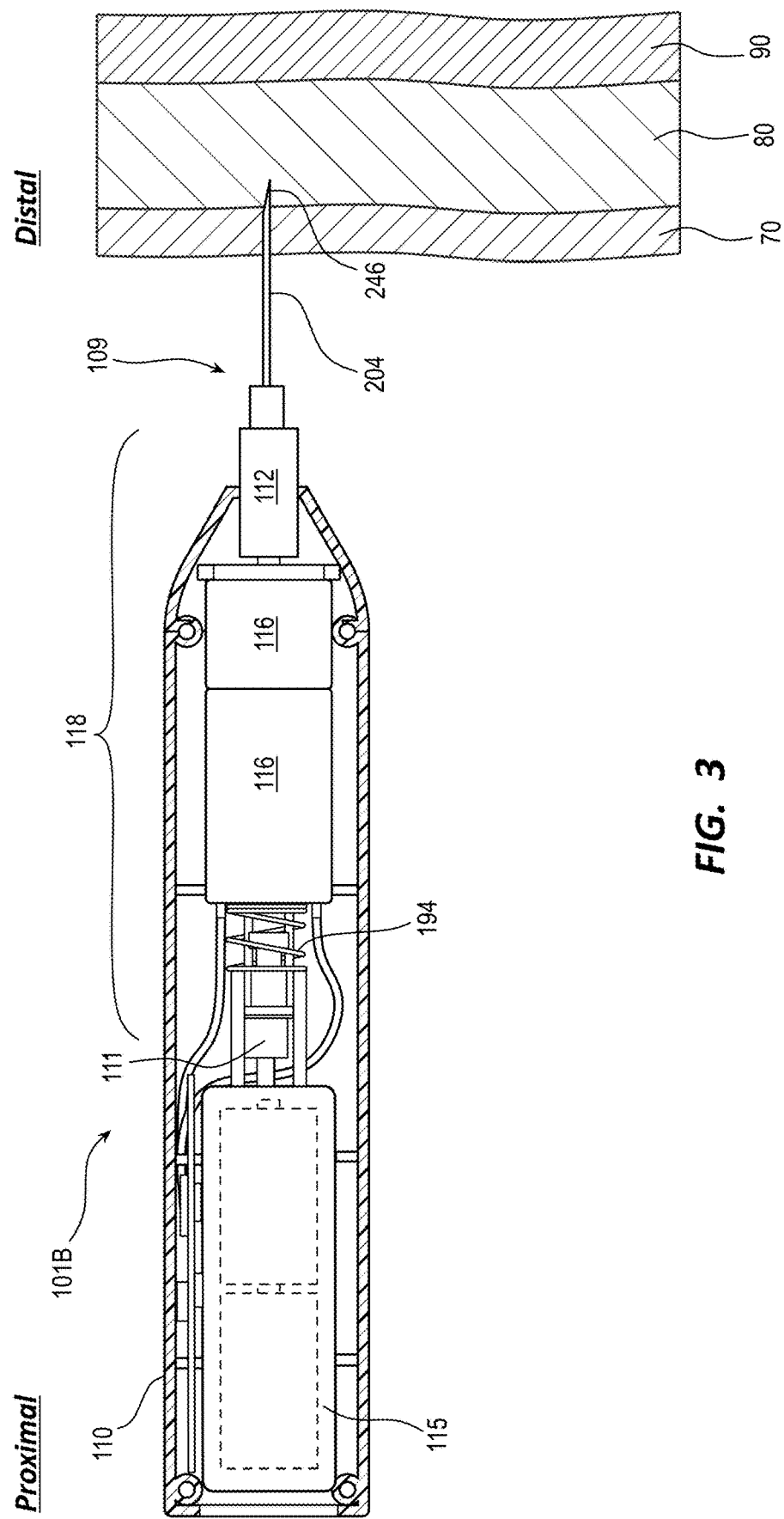
FIG. 3 illustrates a cross-sectional view of an intraosseous access system, in accordance with embodiments disclosed herein.

In an embodiment, the driver 101 can be configured in a variety of compact or ergonomic shapes. For example, user-actuated triggers, i.e. devices that are selective actuated by a user, can be limited to pistol-grip style configurations in order to position the trigger in an accessible position. Automatic, pressure-activated triggers are not reliant on such configurations and can allow for more compact or ergonomic configurations of the system 100. For example, as shown in FIG. 3, a cylindrical driver 101A is provided that defines a substantially tubular shape extending along a longitudinal axis. Such designs can provide more compact drivers 101 than pistol-grip style drivers leading to greater efficiencies in the storage and transport of the devices. These and other ergonomic or compact designs are also contemplated to fall within the scope of the present invention.

In an embodiment, the driver 101 includes a force sensor (not shown), in addition to the activation spring 190, that is configured to automatically stop the driver 101 once the bone cortex 80 has been penetrated. In an embodiment the force sensor is a pressure transducer that detects an axial force applied to the needle tip 246. The force sensor can be configured to detect a presence or absence of axial force applied to the needle tip 246. The system 100 can then determine when the needle tip 246 has penetrated the bone cortex 80 and entered the medullary space 90, and can deactivate the motor 116 to prevent further drilling. Advantageously, the force sensor provides an additional safeguard to prevent back walling. Further, the force sensor can allow a user to selectively activate or deactivate the driver 101 during the placement event, by applying or removing a distal driving force.

In an embodiment, the driver 101 includes a variable speed sensor configured to adjust the speed of the motor 116 proportionally to the amount of distal driving force that is applied to the driver 101. For example, the variable speed sensor is configured to detect the amount of force applied to the driver 101, or amount of deformation applied to the activation spring 190, or the like. The variable speed sensor then increases the speed of the motor proportionally to the amount of force applied or deformation detected. Advantageously, the variable speed sensor balances the correct rotational speed with the amount of distal driving force applied to provide efficient intraosseous placement. This prevents osteonecrosis or back walling, as discussed herein. Advantageously, on activation, the driver 101 can be configured to "ramp up" the motor speed to prevent a sudden start to the activation, which can cause the needle tip 246 to travel away from the selected insertion site leading to misplacement of the access device. Further, the sudden start to the activation can startle the user and also lead to misplacement of the access device.

In an embodiment, the driver 101 includes a timed stop sensor. The timed stop sensor provides an automatic stop after a set amount of time has elapsed since the device was activated. In an embodiment, the timed stop sensor deactivates the motor between 3 seconds and 59 seconds after the motor has been activated. Advantageously, the timed stop sensor provides a safeguard against back walling, by deactivating the motor after a predetermined amount of time has elapsed e.g. 2-3 seconds, or an amount of time required to drill through the bone cortex 80. Further, the timed stop sensor also prevents the battery from being depleted accidentally, for example, during an accidental activation event during storage or transport.

In an embodiment, the driver 101 includes a trigger lock. The trigger lock can include a slide switch, electronic switch, or the like, configured to prevent premature activation of the trigger 111. For example, the trigger lock can be a slide switch configured to inhibit the drive train 118 from transitioning from the distal position to the activated, proximal position. During use, the user can release the trigger lock switch prior to starting the access event. Advantageously, the trigger lock can prevent accidental activation of the driver 101 prior to use, e.g. during transport or storage.

As shown in FIGS. 2A, 2D, in an embodiment, the driver 101 includes a distal driving force indicator 310. The force indicator 310 can include a series of LED lights, a mechanical slider, a rotational dial, combinations thereof, or the like, and include graduated markings 314. The force indicator 310 can include a mechanical or electronic transducer that detects an amount of distal driving force applied to the driver 101 and indicate the amount force, relative to a correct amount of force, which needs to be applied. For example, FIG. 2D shows close up detail of a force indicator 310 that can be disposed on an outer surface of the driver 101. In an embodiment, the drive train 118 can be linked with a slider 312 disposed on an outer surface of the driver 101. As the user applies a distal driving force, the drive train 118 can slide proximally relative to the driver 101, as described herein. The slider 312, coupled with the drive train 118 can also slide proximally relative to the driver housing 108. A series of graduated markings 314 disposed on the driver housing 108, together with the slider 312, can indicate to a user if sufficient distal driving force is being applied, or too much force, or too little force. Advantageously, the force indicator 310 can further guide a user as to the correct operation of the system 100, even if the user has had little or no training. In an embodiment, the force indicator 310 includes a rotational dial that rotates about a series of graduated markings to indicate an amount of force applied. In an embodiment, the force indicator 310 includes one or more LED lights that turn on and off, and/or change color, to indicate an amount of force applied. These and similar configurations of mechanical or electronic force indicators are considered to fall within the scope of the present invention.

Figure 4:
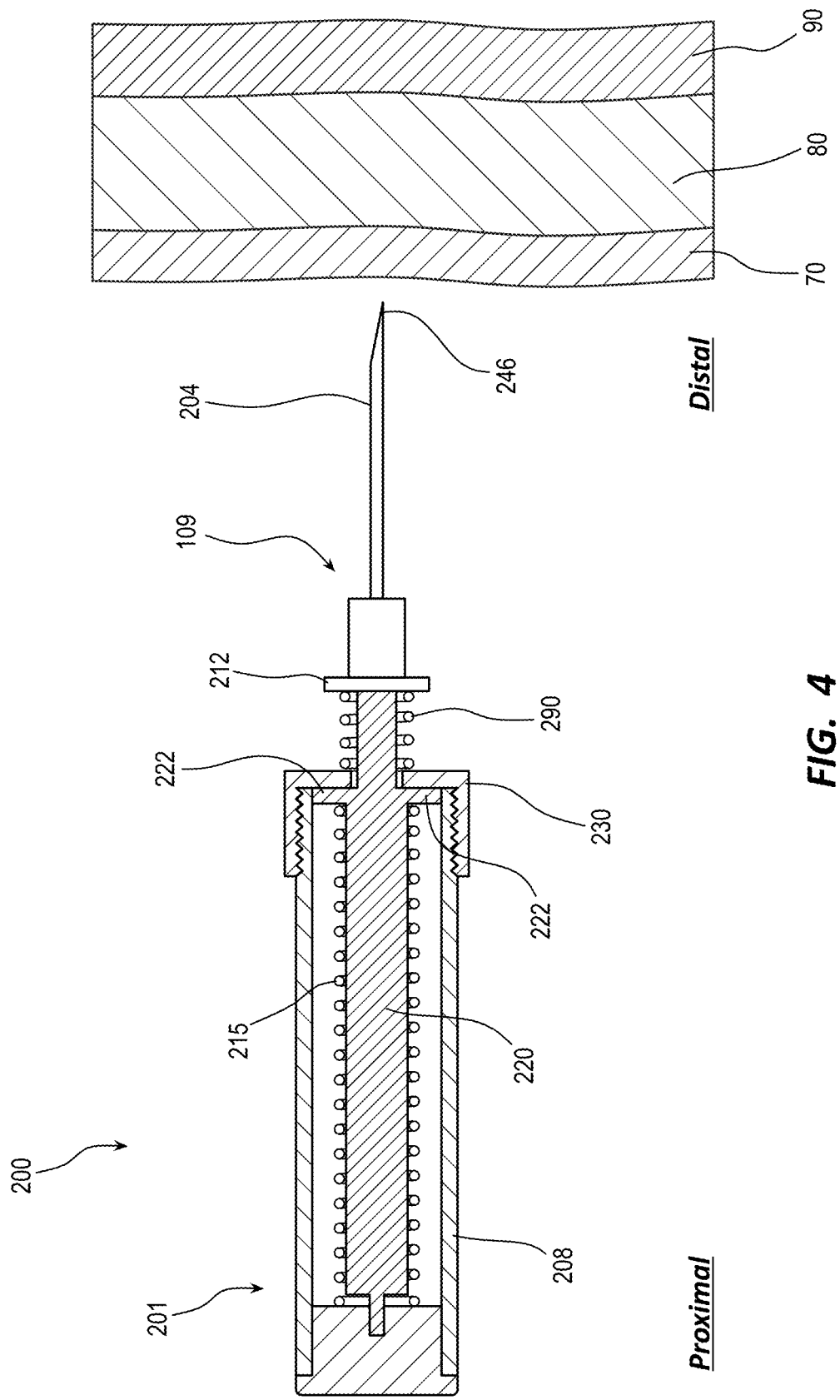
FIG. 4 illustrates a cross-sectional view of a spring-driven intraosseous access device, in accordance with embodiments disclosed herein.

As shown in FIG. 4, in an embodiment, an intraosseous access system 200 generally includes a spring driven energy source 215, and a force actuation spring 290. The access system 200, includes a driver 201 having a driver housing 208 defining a substantially cylindrical shape, although other shaped housings 208 are also contemplated. The access system 200 further includes a spring driven energy source 215 and a drive spindle 220, disposed within the driver housing 208. The drive spindle 220 is configured to rotate about a longitudinal axis of the driver 201. The drive spindle 220 is further configured to slide along a longitudinal axis between a distal, locked position, and a proximal unlocked position, as described in more detail herein. The drive spindle 220 further includes a locking flange 222 that is configured to engage the driver housing 208 when the drive spindle 220 is in the distal, locked position, and disengage the driver housing 208 when the driver spindle 220 is in the proximal unlocked position, as described in more detail herein.

The spring driven energy source ("drive spring") 215 can include a torsion spring configured to store rotational potential energy. However, it will be appreciated that other biasing members are also contemplated. The drive spring 215 can be coupled with both the driver housing 208 and the drive spindle 220 in a tensioned state. As such, when the locking flange 222 disengages the driver housing 208, allowing the drive spindle 220 to rotate freely, the drive spring 215 causes the drive spindle 220 to rotate about the longitudinal axis.

In an embodiment, the driver 201 further includes a coupling interface 212 disposed at a distal end of the drive spindle 220 and configured to engage an access assembly 109, as described herein. Rotation of the drive spindle 220 can cause the access assembly 109 to rotate and causes the needle 204 to drill through the bone cortex 80, and access the medullary cavity 90, as described herein. As used herein, the drive spring 215, drive spindle 220, locking flange 222, coupling interface 212, or combinations thereof can be collectively termed a drive train assembly.

In an embodiment, the driver housing 208 includes a tensioning nut 230 threadably engaged with the driver housing 208. Rotating the tensioning nut 230 about the longitudinal axis, can cause the nut 230 to move along the longitudinal axis relative to the driver housing 208. In an embodiment, the driver 201 includes a force activation spring 290, disposed annularly about the drive spindle 220, between the tensioning nut 230 and the coupling interface 212. In an embodiment, the activation spring 290 is a compression spring, configured to resist a compressive force before deforming. In an embodiment, the compressive force required to deform the spring is between 2-4 lbs of force, although greater or lesser forces are also contemplated. In an embodiment, rotating the tensioning nut 230 can modify the amount of compressive force required to deform the activation spring 290. In an embodiment, the activation spring 290 is configured to bias the drive spindle 220 towards the distal locked position. When a proximal force is applied to the needle tip 246, sufficient to compress the activation spring 290, the drive spindle 220 can move to the proximal unlocked position, activating the device.

In an embodiment, the coupling interface 212 is threadably engaged with drive spindle 220, such that rotating the coupling interface 212 about the longitudinal axis causes the coupling interface 212 to move longitudinally relative to the drive spindle 220. As such, rotating the coupling interface 212 can modify the tension of the activation spring 290 disposed between the coupling interface 212 and the driver housing 208 or tensioning nut 230.

In an embodiment, the locking flange 222 can include one or more locking features configured to allow the locking flange 222 to selectively engage or disengage the driver body 208. FIGS. 5A-5H show some exemplary embodiments of locking features. In an embodiment the flange 222 can include a first, flange locking feature, e.g. flange ratchet teeth 224, configured to selectively engage a second, driver locking feature, e.g. housing ratchet teeth 234, to selectively inhibit relative movement therebetween.

As shown in FIGS. 5A-5B, in an embodiment, the locking flange 222 includes a plurality of ratchet teeth 224 that are configured to engage a plurality of housing ratchet teeth 234 disposed on the housing 208, tensioning nut 230, or combinations thereof. The flange ratchet teeth 224 and housing ratchet teeth 234 are configured to engage to inhibit rotational movement of the drive spindle 222 about the longitudinal axis in a first direction, e.g. a clockwise direction, and configured to allow stepwise rotation in a second, opposite, direction, e.g. anti-clockwise direction. Advantageously, this allows the drive spring 215 to be tensioned by rotating the drive spindle 220 in the second direction. The system 200 maintains the tension by the engagement of the flange ratchet teeth 224 and housing ratchet teeth 234 to prevent rotation in the first direction. In an embodiment, when a proximal force is applied to the needle tip 246, which is sufficient to overcome the compression force of the activation spring 290, the spindle 220 and locking flange 222 move proximally and disengage the flange ratchet teeth 224 from the housing ratchet teeth 234 to allow free rotation of the spindle 220. The drive spring 215 then causes the drive spindle 220 to rotate as described herein.

As shown in FIGS. 5C-5D, in an embodiment, the drive spindle 220 includes one or more lugs 226 that engage one or more detents 236 disposed within the housing 208, tension nut 230, or combinations thereof. As shown in FIG. 5C, the lugs 226 engage the detents 236 and prevent rotational movement of the drive spindle 220. In an embodiment, when a proximal force is applied to the needle tip 246, which is sufficient to overcome the compression force of the activation spring 290, the spindle 220 and locking flange 222 move proximally and disengage lugs 226 from the detents 236 to allow free rotation of the spindle 220. The drive spring 215 then causes the drive spindle 220 to rotate as described herein.

As shown in FIGS. 5E-5F, in an embodiment, the locking flange 222 includes a frangible bridge 228 that is formed between the locking flange 222 and the housing 208, tension nut 230, or combinations thereof. The frangible bridge 228 can include a tear line, e.g. a score line, laser cut line, perforation, or the like, that is configured to break when a predetermined force is applied, allowing the locking flange 222 to separate from the housing body 208 or tension nut 230. For example, when a proximal force is applied to the needle tip 246, which is sufficient to overcome the force required for the breach line to separate, the frangible bridge 228 detaches from the housing 208/tension nut 230, allowing the spindle 220 and locking flange 222 move proximally and to allow free rotation of the spindle 220. The drive spring 215 then causes the drive spindle 220 to rotate as described herein. In an embodiment, the frangible bridge 228 can be used in place of the activation spring 290 to prevent proximal movement until sufficient proximal force is applied. In an embodiment, the frangible bridge 228 can be used in addition to the activation spring 290 to prevent proximal movement until sufficient proximal force is applied.

As shown in FIGS. 5G-5H, in an embodiment, the driver 201 includes a locking lever 240, configured to engage the locking flange 222, drive spindle 220, or combinations thereof to prevent the drive spindle 220 from rotating. In an embodiment, an outer surface of the locking flange 222 includes one or more locking teeth. The locking lever 240 engages the locking teeth and prevents the drive spindle 220 from rotating. In an embodiment, when a proximal force is applied to the needle tip 246, which is sufficient to overcome the compression force of the activation spring 290, the spindle 220 moves proximally. As shown in FIG. 5H, a portion of the locking lever 240 is actuated by the proximal movement of the drive spindle 220 and causes the locking lever 240 to pivot and disengage from the locking flange 222 to allow free rotation of the spindle 220. The drive spring 215 then causes the drive spindle 220 to rotate as described herein.

In an exemplary method of use a spring driven intraosseous access system 200 is provided, as described herein, including a coiled drive spring 215 and an activation spring 290. A user urges the driver 201 distally until a needle tip 246 penetrate a skin surface 70. To note, the resistance of the needle 204 penetrating the skin tissues 70 is less than a force required to deform the activation spring 290. As such the drive spindle 220 and access assembly 190 remains a distal, locked position. The needle tip 246 then contacts the bone cortex 80, a user can continue to urge the driver 201 distally with sufficient force to deform the activation spring 290 by pressing the access assembly 109 into the bone cortex 80. The access assembly 109 and driver spindle 220 slides proximally relative to the driver housing 208, compressing the activation spring 290 between the coupling interface 212 and the tensioning nut 230 portion of the driver housing 208. The locking flange 222, coupled to the driver spindle 220, disengages from the driver housing 208 allowing the driver spindle 220 to rotate. The drive spring 215 causes the driver spindle 220 and access assembly 109 to rotate, drilling the needle 204 into the bone cortex 80 and accessing the medullary cavity.

Figures 6A, 6B:
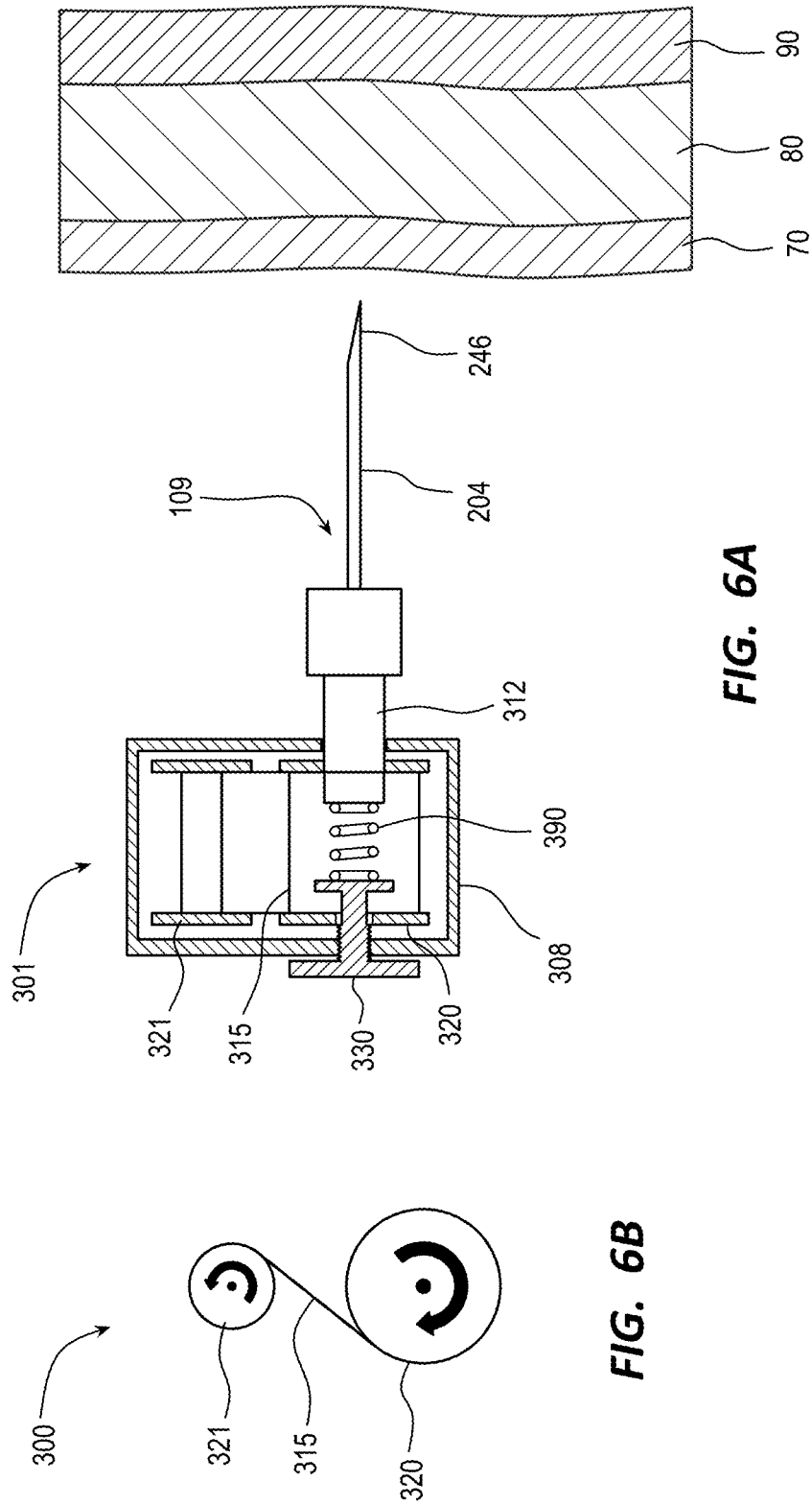
FIG. 6A illustrates a cross-sectional view of a spring-driven intraosseous access device, in accordance with embodiments disclosed herein.
FIG. 6B illustrates a schematic view of the spring drive of the spring-driven intraosseous access device for FIG. 6A, in accordance with embodiments disclosed herein.

As shown in FIGS. 6A-6B, in an embodiment, an intraosseous access system 300 is provided including a flat drive spring 315. The access system 300, includes a driver 301 having a driver body 308, with a flat drive spring 315, a drive spindle 320, and a collector spindle 321, disposed therein.

In a tensioned state, the drive spring 215 is wrapped about the drive spindle 220. As the drive spring transitions between a tensioned state and an untensioned state, the flat spring unwinds from the drive spindle 320, causing the drive spindle to rotate, and is wound on to the collector spindle 321. FIG. 6B shows a plan view of the drive spindle 320, the collector spindle 321 and the flat drive spring 315 extending therebetween, including the associated direction of rotation for each of the drive spindle 320 and the collector spindle 321. Advantageously, the flat drive spring provides a more constant torque and more constant rotational speed as the spring transitions between a tensioned and an untensioned state.

In an embodiment, the drive spindle 320 and the collector spindle 321 remain in a longitudinally fixed position, relative to the drive body 208. In an embodiment, a coupling interface 312 is slidably engaged with the drive spindle 320 along a longitudinal axis. The coupling interface 312 is also coupled with the drive spindle 320 such that any rotational movement of the drive spindle 320 causes the coupling interface 312 and access assembly 109 to rotate.

In an embodiment, the driver 301 includes an activation spring 390, disposed within the drive spindle 320 and is biased to maintain the coupling interface 312 is a distal position. When a force is applied to a needle tip 246 in a proximal direction, which is sufficient to overcome the force of the activation spring 390, the activation spring 390 can deform and allow the coupling interface 312 to slide longitudinally. The coupling interface can further include a locking flange, as described herein. As the coupling interface 312 transitions from a distal position to a proximal position, the locking flange can disengage allowing the coupling interface 312 and drive spindle 320 to rotate. The coupling interface 312 and locking flange can include various ratchet teeth, lugs and detents, frangible bridges, locking levers, combinations thereof, or the like, as described herein, to selectably inhibit rotation of the coupling interface 312 and drive spindle 320 assembly until activated.

In an embodiment, the driver 301 further includes a tensioning nut 330, which is threadably engaged with the driver housing 208. As such, rotating the tensioning nut 330 about the longitudinal axis can modify the tension of the activation spring 390 which can modify the amount of force required to move the access assembly 109 longitudinally and trigger the device 300.

In an exemplary method of use a spring driven intraosseous access system 300 is provided, as described herein, including a flat drive spring 315 and an activation spring 390. A user urges the driver 301 distally until a needle tip 346 penetrates a skin surface 70. To note, the resistance of the needle 304 penetrating the skin tissues 70 is less than a force required to deform the activation spring 390. As such the activation spring 390 maintains the coupling interface 312 and access assembly 190 in a distal, locked position. The needle tip 246 then contacts the bone cortex 80 where the resistance to needle penetration is greatly increased. A user can continue to urge the driver 301 distally with sufficient force to deform the activation spring 390 by pressing the access assembly 109 into the bone cortex 80. The access assembly 109 and coupling interface 312 slides proximally relative to the driver housing 308, compressing the activation spring 390 between the coupling interface 312 and the tensioning nut 330. The locking feature, which is configured to inhibit rotation of the coupling interface 312, disengages from the driver housing 308 allowing the coupling interface 312 and access assembly 109 to rotate, drilling the needle 304 into the bone cortex 80 and accessing the medullary cavity 90.

Advantageously, the drive springs disclosed herein, e.g. drive spring 215, 315, can maintain the stored energy of over an extended period of time without depleting. Further, these drive springs include an inherent time stop feature to prevent backwalling, as described herein. i.e. The drive spring 215 can be configured to provide sufficient rotations of the access assembly to drill through the bone cortex before reaching an untensioned state and ceasing further drilling. In an embodiment, the drive springs are configured to provide between 10-20 rotations to provide sufficient drilling to penetrate the bone cortex and access the medullary cavity without backwalling. It will be appreciated, however, that the drive springs can also be configured to provide fewer or greater numbers of rotations.

Figure 6C:
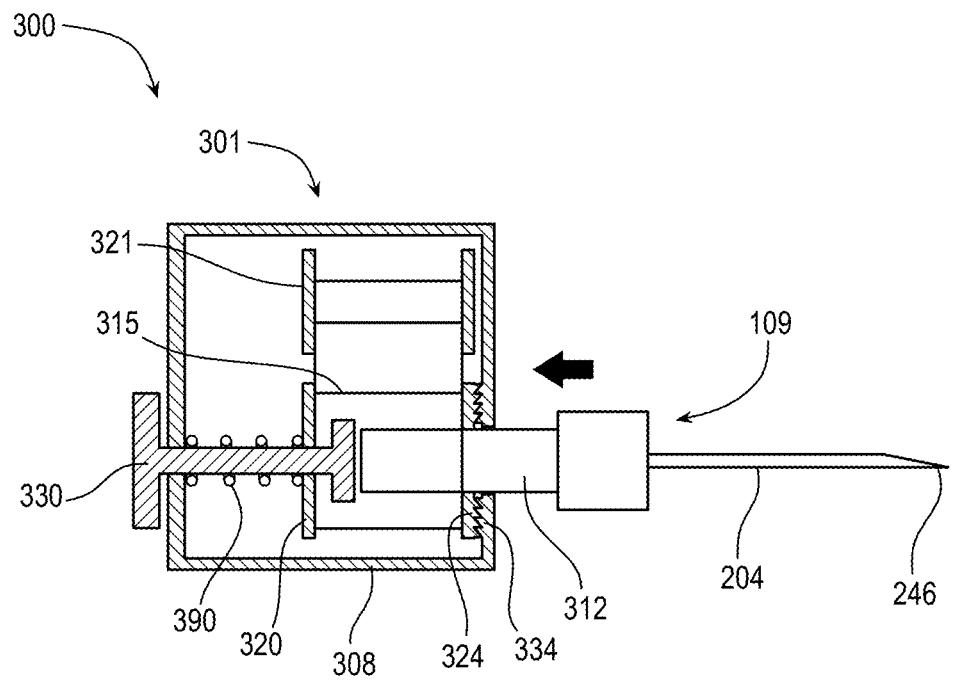
FIGS. 6C-6D illustrate cross-sectional views of a spring-driven intraosseous access device, in accordance with embodiments disclosed herein.
Figure 6D:
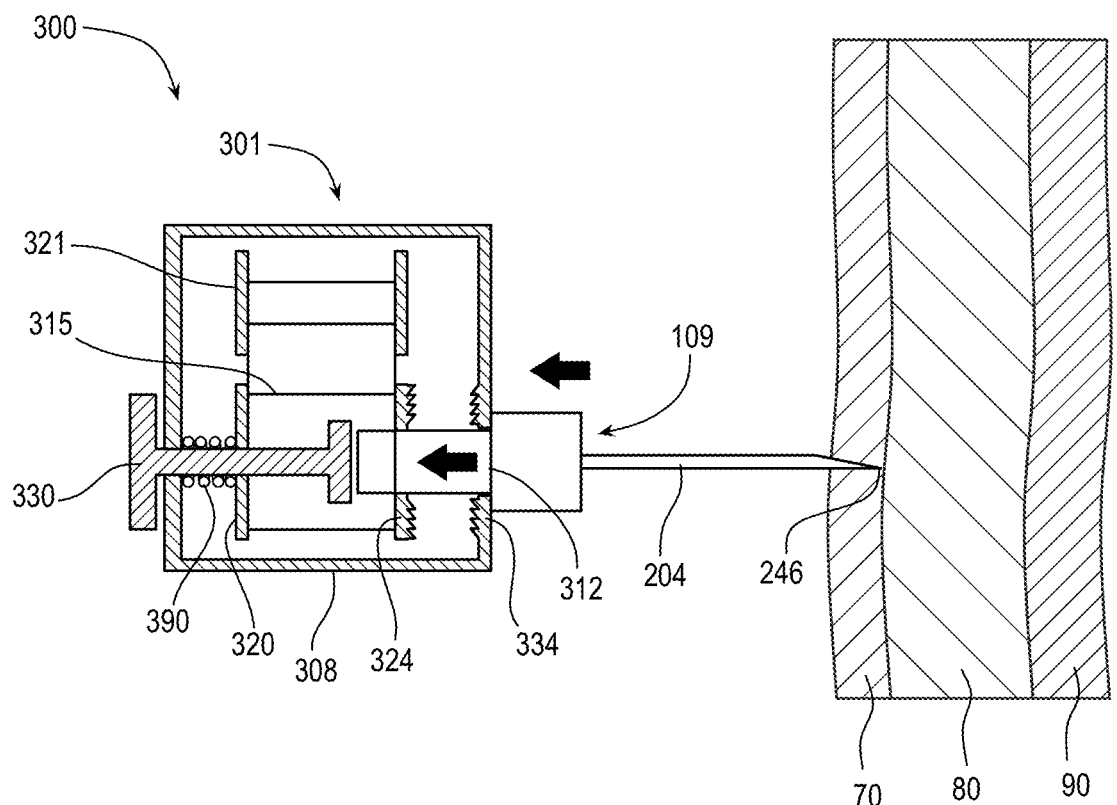

In an embodiment, as shown in FIGS. 6C-6D, the drive train can include a drive spindle 320, drive spring 315, collector spindle 321, and access assembly 109. The drive train can be slidably engaged relative to the housing 308 along a longitudinal axis, as described herein. The activation spring 390 can be disposed between the drive train, e.g. the drive spindle 320, and the housing 308 and can bias the drive train towards a distal position (FIG. 6C). In an embodiment, one of the drive spindle 320 or the collector spindle 321 can include a locking engagement feature, as described herein, configured to selectively inhibit rotation of the drive spindle 320. For example, as shown in FIG. 6C, the drive spindle can include a first set of ratchet teeth 324 disposed on the drive spindle 320 configured to engage a second set of ratchet teeth 334 disposed on the housing 308 in the distal position. As shown in FIG. 6D an axial force applied to the access assembly 109 can compress the activation spring 390, allowing the drive train to transition to the proximal position. This in turn can allow the first set of ratchet teeth 324 to disengage the second set of ratchet teeth 334 and allow the drive spindle 320 to rotate, as described herein.

Figure 6E:
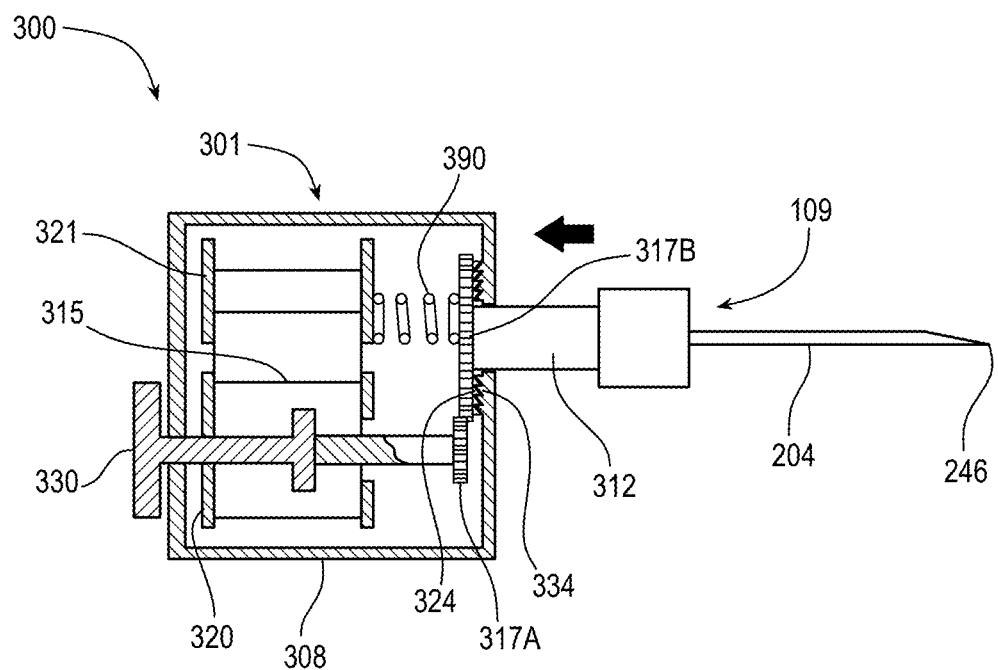
FIGS. 6E-6F illustrate cross-sectional views of a geared, spring-driven intraosseous access device, in accordance with embodiments disclosed herein.
Figure 6F:
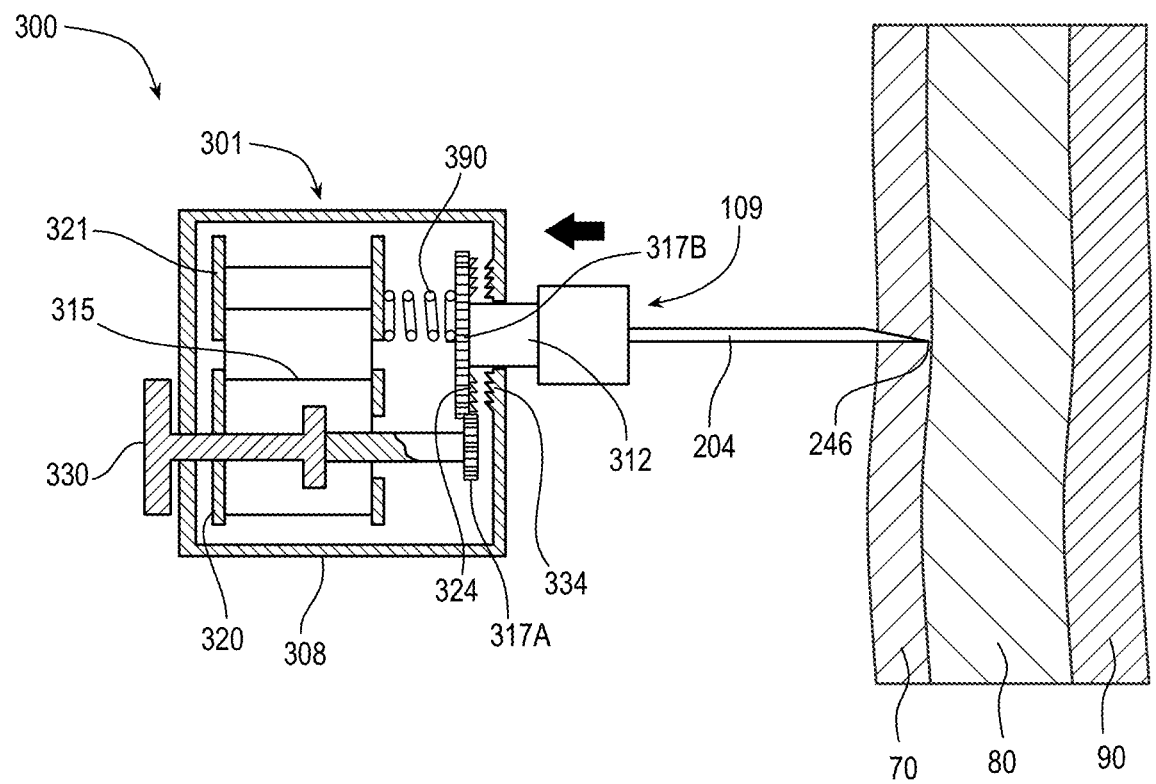

In an embodiment, as shown in FIGS. 6E-6F, the drive train can include the drive spindle 320, drive spring 315, collector spindle 321, and access assembly 109, and can further include a gear mechanism 317. The gear mechanism 317 can either be "geared up" or "geared down" to modify one of the speed or torque of the access assembly 109 relative to the rotation speed of the drive spindle 320. The gear mechanism 317 can include spur gears, planetary gears, helical gears, bevel gears, miter gears, worm gears, screw gears, combinations thereof, or the like.

In an embodiment, the gears within the gear mechanism 317 can slide along the longitudinal axis relative to each other. As such, when an axial force is applied to the access assembly 109, the access assembly 109 and gear(s) 317B coupled thereto can slide longitudinally from the distal position to the proximal position. The drive spindle 320 and gear(s) 317A coupled thereto and remain stationary relative to the longitudinal position. The movement of the access assembly 109 and gear(s) 317B can disengage a locking feature, e.g. ratchet teeth 324, 334 and can allow the gear mechanism 317, drive spindle 320 and access assembly 109 to rotate, as described herein. The system 300 can further include an activation spring 390 configured to bias the access assembly 109 and gear(s) 317B towards the distal, locked position. In an embodiment the locking feature can be configured to engage the drive gear 317A coupled with the drive spindle 320.

In an embodiment, a gear ratio between the drive spindle 320 and the access assembly 109 can be greater than 1.0. Further the locking feature can be configured to engage the driven gear 317B coupled to the access assembly 109. Advantageously, the force required by the locking feature to engage and inhibit movement of the driven gear 317B can be less than the force required to engage and inhibit movement of the drive gear 317A where the drive ratio is greater than 1.0.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of placing an intraosseous access assembly, comprising:
   providing an intraosseous access device, comprising:
   a driver,
   a drive train assembly, wherein a portion of the drive train assembly is configured to be transitionable between a first position and a second position,
   a force indicator being a series of lights and configured to indicate an amount of force exerted on the drive train assembly,
   an access assembly coupled to the drive train assembly and including a needle, and
   a time out sensor configured to cease rotation of the access assembly after a predetermined amount of time has elapsed;
   providing a first force to urge the access assembly distally until a tip of the needle penetrates a skin surface and contacts a bone cortex;
   providing a second force to urge the access assembly distally and transition the portion of the drive train assembly from the first position to the second position;
   rotating the access assembly; and
   drilling the needle through the bone cortex.

2. The method according to claim 1, wherein the drive train assembly includes one of a power source, an electronic control board, an electric motor, a gear assembly, or a coupling interface including a socket that defines a cavity.

3. The method according to claim 2, wherein the power source further includes a replaceable rechargeable battery pack or a replaceable non-rechargeable battery pack.

4. The method according to claim 1, wherein the drive train assembly includes one of a drive spring, a drive spindle, a locking flange, or a coupling interface including a socket that defines a cavity.

5. The method according to claim 4, wherein the drive spring includes one of a torsion spring or a flat spring.

6. The method according to claim 4, wherein the locking flange is coupled to the drive spindle and engaged with the driver with a frangible bridge to inhibit axial rotation of the drive spindle when in the first position.

7. The method according to claim 6, wherein the frangible bridge includes a tear line configured to break when a predetermined force is applied and transition the drive spindle to the second position.

8. The method according to claim 7, wherein the tear line includes one of a score line, a laser cut line, or a perforation.

9. The method according to claim 1, wherein the intraosseous access device further includes an activation biasing member configured to bias the portion of the drive train assembly towards the first position, wherein the activation biasing member includes an activation spring, and wherein a force required to deform the activation biasing member is greater than the first force and less than the second force.

10. The method according to claim 9, wherein the intraosseous access device further includes a tensioning nut configured to adjust a tension of the activation biasing member.

11. The method according to claim 1, wherein the intraosseous access device further includes one or more of a variable speed sensor, a battery charge indicator, a trigger lock, or a force sensor.

12. The method according to claim 11, wherein the variable speed sensor is configured to modify a speed of an electric motor of the intraosseous access device according to an amount of distal driving force applied to the access assembly.

13. The method according to claim 11, wherein the battery charge indicator is disposed on a power source.

14. The method according to claim 11, wherein the trigger lock is transitionable between a locked position and an unlocked position, wherein the trigger lock is configured to inhibit the portion of the drive train assembly from transitioning to the second position when in the locked position.

15. The method according to claim 14, wherein the trigger lock includes one of a slide switch or an electronic switch.

16. The method according to claim 11, wherein the force sensor is a pressure transducer configured to detect a presence or an absence of an axial force applied to a needle tip.

17. The method according to claim 1, wherein the driver is cylindrical and defines a substantially tubular shape extending along a longitudinal axis.

18. The method according to claim 1, wherein a series of lights of the force indicator includes a series of light emitting diodes (LEDs).

19. The method according to claim 1, wherein the first force is between 2 pounds and 4 pounds of force.

* * * * *